(12) United States Patent
Niven et al.

(10) Patent No.: US 11,986,615 B2
(45) Date of Patent: *May 21, 2024

(54) SYSTEM FOR PUNCTURING THE EPIDERMIS WITH CONTROLLED FLUID DELIVERY

(71) Applicant: Rejuvatek Medical, Inc., Sandy, UT (US)

(72) Inventors: Gregg D Niven, Kaysville, UT (US); Joseph D Niven, Bountiful, UT (US); Timothy N Turner, West Jordan, UT (US); Jack H Savage, Sandy, UT (US)

(73) Assignee: Rejuvatek Medical, Inc., Sandy, UT (US)

( * ) Notice: Subject to any disclaimer, the term of this patent is extended or adjusted under 35 U.S.C. 154(b) by 474 days.

This patent is subject to a terminal disclaimer.

(21) Appl. No.: 17/245,921

(22) Filed: Apr. 30, 2021

(65) Prior Publication Data
US 2021/0244496 A1 Aug. 12, 2021

Related U.S. Application Data

(63) Continuation of application No. 15/261,665, filed on Sep. 9, 2016, now Pat. No. 11,020,203.
(Continued)

(51) Int. Cl.
*A61M 37/00* (2006.01)
*A61B 17/00* (2006.01)
(Continued)

(52) U.S. Cl.
CPC ......... *A61M 37/0084* (2013.01); *A61B 17/00* (2013.01); *A61B 90/39* (2016.02);
(Continued)

(58) Field of Classification Search
CPC ............... A61M 37/0084; A61M 5/46; A61M 2210/04; A61B 90/39; A61B 2090/395;
(Continued)

(56) References Cited

U.S. PATENT DOCUMENTS 2,588,623 A 3/1952 Eliscu
6,505,530 B2 1/2003 Adler et al.
(Continued)

OTHER PUBLICATIONS

"Manual for Dragonfly X2 Tattoo Machine" InkMachines, (May 7, 2010), 33 pages, available at http://www.inkmachines.com/sites/default/files/files/Manual_For_Dragonfly_X2_tattoo_machine_EN_rev1.pdf.

*Primary Examiner* — David B. Thomas
(74) *Attorney, Agent, or Firm* — Gurr Brande & Spendlove, PLLC; Robert Spendlove

(57) ABSTRACT

Embodiments of an actuating device for actuating a needle cartridge and puncturing an epidermis with controlled depth. The actuating device includes a motor housed in a motor housing, an actuating rod driven by the motor and configured to actuate in a reciprocating motion, and an adjustment mechanism. The actuating rod is housed in a rod housing, the rod housing forming a device aperture configured to receive a needle cartridge and to attach to the needle cartridge. The adjustment mechanism interfaces with the rod housing and is configured to adjust a position of the rod housing relative to the motor housing while not rotating the rod housing relative to the motor housing.

18 Claims, 16 Drawing Sheets

Related U.S. Application Data

(60) Provisional application No. 62/216,206, filed on Sep. 9, 2015.

(51) Int. Cl.
*A61B 34/10* (2016.01)
*A61B 90/00* (2016.01)
*A61M 5/46* (2006.01)

(52) U.S. Cl.
CPC ..... *A61M 5/46* (2013.01); *A61B 2017/00769* (2013.01); *A61B 2034/102* (2016.02); *A61B 2090/395* (2016.02); *A61M 2210/04* (2013.01)

(58) Field of Classification Search
CPC .......... A61B 17/00; A61B 2017/00769; A61B 2034/102
See application file for complete search history.

(56) References Cited

U.S. PATENT DOCUMENTS

| | | |
|---|---|---|
| 6,585,694 B1 | 7/2003 | Smith et al. |
| 8,663,162 B2 | 3/2014 | Bunting et al. |
| 8,920,379 B2 | 12/2014 | Lee |
| 9,707,385 B1 | 7/2017 | Chen et al. |
| 9,750,528 B2 | 9/2017 | Scherkowski |
| 11,020,203 B2 * | 6/2021 | Niven ................ A61M 37/0084 |
| 11,529,505 B2 * | 12/2022 | Niven .................... A61B 90/39 |
| 2002/0069726 A1 | 6/2002 | Adler et al. |
| 2002/0193752 A1 | 12/2002 | Lynn |
| 2003/0171767 A1 | 9/2003 | Koplen |
| 2003/0195542 A1 | 10/2003 | Lee |
| 2004/0186501 A1 | 9/2004 | Su |
| 2005/0010236 A1 | 1/2005 | Frister |
| 2005/0107738 A1 | 5/2005 | Slater et al. |
| 2008/0208235 A1 | 8/2008 | Ulmer et al. |
| 2008/0221548 A1 | 9/2008 | Danenberg et al. |
| 2008/0287978 A1 | 11/2008 | Hickman |
| 2009/0125050 A1 | 5/2009 | Dixon |
| 2012/0041374 A1 | 2/2012 | Lee |
| 2015/0202420 A1 | 7/2015 | Miller et al. |
| 2016/0263365 A1 | 9/2016 | Smith |

* cited by examiner

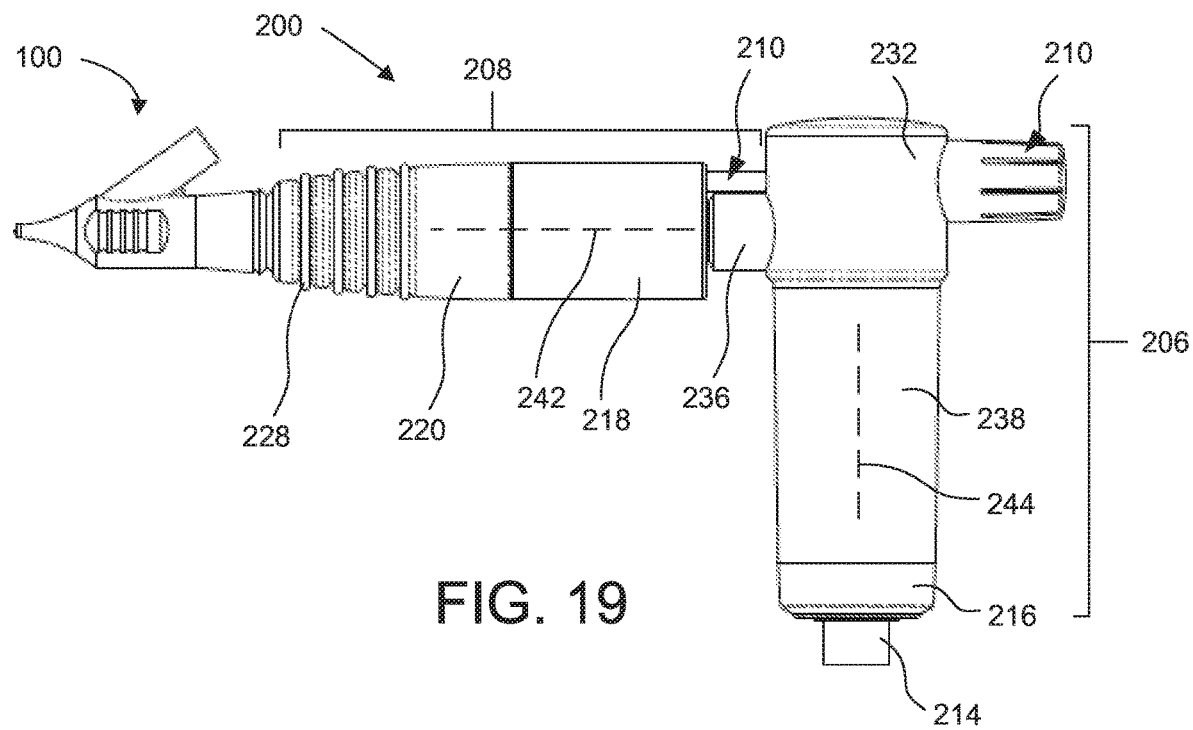
FIG. 19
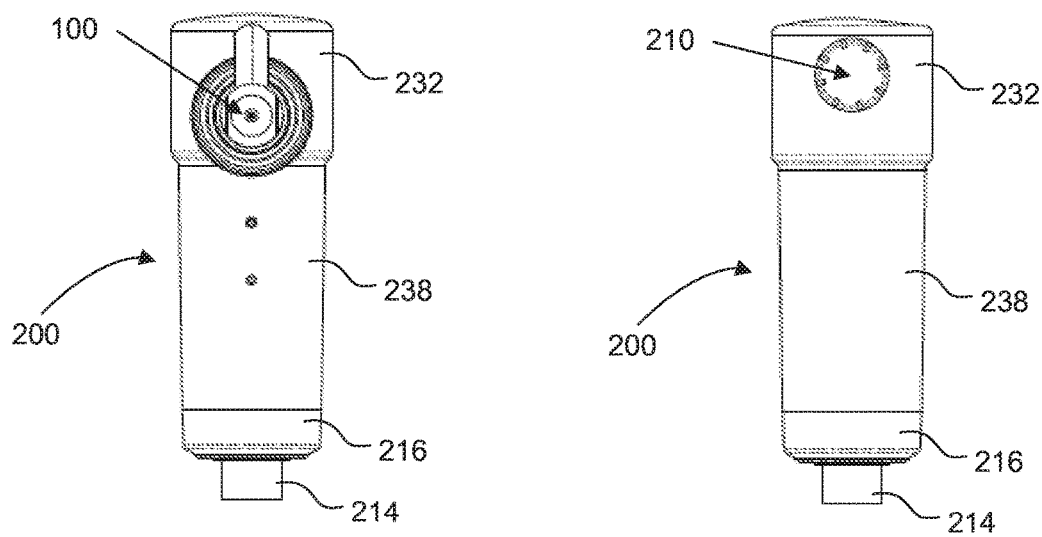
FIG. 20
FIG. 21

SYSTEM FOR PUNCTURING THE EPIDERMIS WITH CONTROLLED FLUID DELIVERY

CROSS-REFERENCE TO RELATED APPLICATIONS

This application is a continuation of U.S. patent application Ser. No. 15/261,665 filed on Sep. 9, 2016, and entitled "System for Puncturing the Epidermis with Controlled Fluid Delivery," which claims the benefit of U.S. Provisional Patent Application Ser. No. 62/216,206 filed on Sep. 9, 2015, and entitled "Tattoo and Tattoo Removal Device and Method," the contents of both of which are hereby incorporated by reference herein.

BACKGROUND

Tattooing is the process of the introduction of colored inks into the dermis layer of skin to permanently color the skin. The process requires the controlled application of the colored inks to the dermis layer of a patient's skin, by repeatedly perforating the epidermis layer of skin with controlled punctures by needles coated in ink. Once punctured, the skin cells wipe the ink from the surface of the needles, which essentially stains these cells with the desired pigments.

Tattoos (as well as permanent make-up) can over time be less desirable for people due to poor design, social stigma, or life changes (e.g., career or relationship changes, etc.). Tattoo removal can be difficult, costly, and painful. Improvements in tattoo removal are needed to better serve a large segment of customers with a less difficult, costly, and painful removal process.

SUMMARY

The subject matter of the present application has been developed in response to the present state of the art, and in particular, in response to the shortcomings of tattoo removal, that have not yet been fully solved by currently available techniques. Accordingly, the subject matter of the present application has been developed to overcome at least some of the shortcomings of prior art techniques.

Embodiments of an actuating device for actuating a needle cartridge and puncturing an epidermis with controlled depth are described. In one embodiment, the actuating device includes a motor housed in a motor housing, an actuating rod driven by the motor and configured to actuate in a reciprocating motion, and an adjustment mechanism. The actuating rod is housed in a rod housing, the rod housing forming a device aperture configured to receive a needle cartridge and to attach to the needle cartridge. The adjustment mechanism interfaces with the rod housing and is configured to adjust a position of the rod housing relative to the motor housing while not rotating the rod housing relative to the motor housing. Other embodiments of an actuating device are described.

Embodiments of a system are described. In one embodiment, the system includes an actuating device and a needle cartridge. The actuating device includes a motor housed in a motor housing, an actuating rod driven by the motor and configured to actuate in a reciprocating motion, and an adjustment mechanism. The actuating rod is housed in a rod housing, the rod housing forming a device aperture configured to receive a needle cartridge and to attach to the needle cartridge. The adjustment mechanism interfaces with the rod housing and is configured to adjust a position of the rod housing relative to the motor housing while not rotating the rod housing relative to the motor housing. The needle cartridge includes a cartridge housing, a needle group assembly, and a fluid port. The cartridge housing forms a cavity and includes a first aperture and a second aperture opposite the first aperture. The needle group assembly includes a needle and a needle holder. The needle group assembly is configured to move in a reciprocating motion relative to the housing along an axis from the first aperture to the second aperture. During the reciprocating motion, the needle fully retracts into the cavity through the first aperture. The fluid port is integrated with the housing and includes a hollow projection forming a conduit and extending away from the housing. The fluid port includes a third aperture, wherein the fluid port is configured to interface with a fluid delivery system.

Embodiments of a method are described. In one embodiment, the method includes actuating a push rod of an actuating device. The actuating device includes a motor housed in a motor housing, an actuating rod driven by the motor and configured to actuate in a reciprocating motion, and an adjustment mechanism. The actuating rod is housed in a rod housing, the rod housing forming a device aperture configured to receive a needle cartridge and to attach to the needle cartridge. The adjustment mechanism interfaces with the rod housing and is configured to adjust a position of the rod housing relative to the motor housing while not rotating the rod housing relative to the motor housing. The method further includes adjusting the position of the rod housing relative to the motor housing without rotating the rod housing relative to the motor housing. Other embodiments of the method are described herein.

Other aspects and advantages of embodiments of the present invention will become apparent from the following detailed description, taken in conjunction with the accompanying drawings illustrated by way of example of the principles of the invention.

The described features, structures, advantages, and/or characteristics of the subject matter of the present disclosure may be combined in any suitable manner in one or more embodiments and/or implementations. In the following description, numerous specific details are provided to impart a thorough understanding of embodiments of the subject matter of the present disclosure. One skilled in the relevant art will recognize that the subject matter of the present disclosure may be practiced without one or more of the specific features, details, components, materials, and/or methods of a particular embodiment or implementation. In other instances, additional features and advantages may be recognized in certain embodiments and/or implementations that may not be present in all embodiments or implementations. Further, in some instances, well-known structures, materials, or operations are not shown or described in detail to avoid obscuring aspects of the subject matter of the present disclosure. The features and advantages of the subject matter of the present disclosure will become more fully apparent from the following description and appended claims, or may be learned by the practice of the subject matter as set forth hereinafter.

BRIEF DESCRIPTION OF THE DRAWINGS

In order that the advantages of the subject matter may be more readily understood, a more particular description of the subject matter briefly described above will be rendered by reference to specific embodiments that are illustrated in the appended drawings. Understanding that these drawings depict only typical embodiments of the subject matter and are not therefore to be considered to be limiting of its scope, the subject matter will be described and explained with additional specificity and detail through the use of the drawings.

FIG. 19 depicts a side view of an actuating device and an attached needle cartridge, according to one or more embodiments of the present disclosure.

FIG. 20 depicts a front view of an actuating device and an attached needle cartridge, according to one or more embodiments of the present disclosure.

FIG. 21 depicts a rear view of an actuating device and an attached needle cartridge, according to one or more embodiments of the present disclosure.

Figure 1:
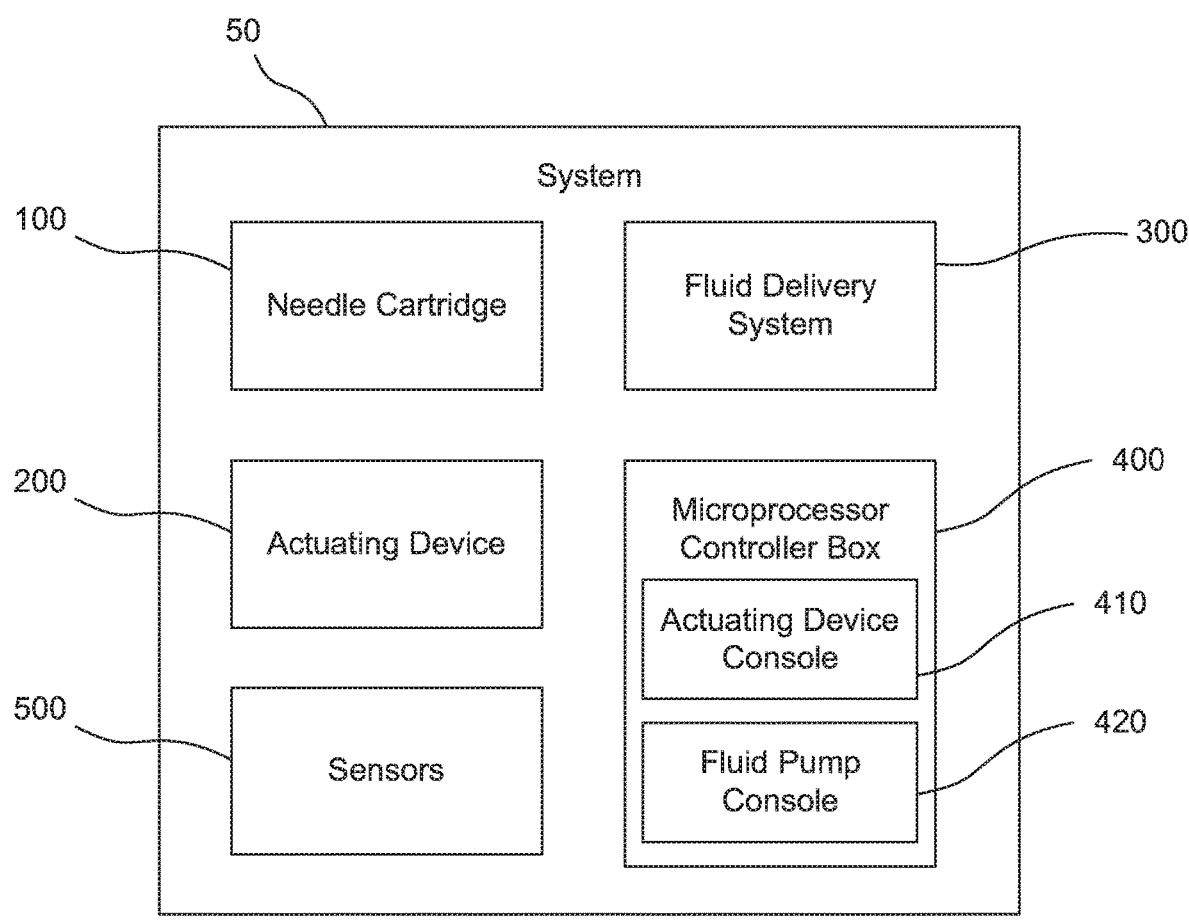
FIG. 1 depicts a schematic diagram of a system for puncturing the epidermis with controlled fluid delivery, according to one or more embodiments of the present disclosure.

It will be appreciated that the drawings are illustrative and not limiting of the scope of the invention which is defined by the appended claims. The embodiments shown accomplish various aspects and objects of the invention. It is appreciated that it is not possible to clearly show each element and aspect of the invention in a single figure, and as such, multiple figures are presented to separately illustrate the various details of the invention in greater clarity. Similarly, not every embodiment need accomplish all advantages of the present invention.

While the disclosure is susceptible to various modifications and alternative forms, specific embodiments have been shown by way of example in the drawings and will be described in detail herein. However, it should be understood that the disclosure is not intended to be limited to the particular forms disclosed. Rather, the intention is to cover all modifications, equivalents and alternatives falling within the spirit and scope of the invention as defined by the appended claims.

Throughout the description, similar reference numbers may be used to identify similar elements.

DETAILED DESCRIPTION

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

While many embodiments are described herein, at least some of the described embodiments allow for the efficient removal of tattoos, permanent makeup, and other indelible mark or pigment on and under the skin. Some embodiments allow for self-cleaning of a needle grouping. Some embodiments provide for more accurate and consistent depth of needle penetration on the skin of a patient. Some embodiments allow for the efficient delivery of fluid with minimal or no leaking of the fluid into the interior of an actuating device. Some embodiments allow for the adjustment of a depth of penetration of needles without rotating the needle cartridge relative to the actuating device.

While description herein refers primarily to tattoo removal, the apparatuses, systems, and methods described herein may be also be utilized for tattooing or other application of inks, etc., to the skin of a patient.

Referring to FIG. 1, a schematic diagram of an embodiment of a system 50 for puncturing the epidermis with controlled fluid delivery is shown. The system 50 includes a needle cartridge 100, an actuating device 200, a fluid delivery system 300, a microprocessor controller 400, and sensors 500 (and sensing circuitry). Although the system 50 for puncturing the epidermis with controlled fluid delivery is shown and described with certain components and functionality, other embodiments of the system 50 for puncturing the epidermis with controlled fluid delivery may include fewer or more components to implement less or more functionality.

In some embodiments, the needle cartridge 100 is configured to attach to the actuating device 200. The actuating device 200 actuates a needle or needle group of the needle cartridge in a reciprocating motion to aid in the placement or removal of tattoos in the skin of a patient. The system 50 further includes a fluid delivery system 300 configured to deliver a fluid to the needle cartridge 100 and out the needle cartridge 100 during the reciprocating motion of the needle or needle group. The fluid may be ink for the placement of a tattoo or may be a cleansing fluid for the removal of a tattoo. The fluid may, in some embodiments, be an eschar-inducing material (EIM) disclosed and described in U.S. Pat. No. 8,663,162 (Tattoo Removal System, '162 patent), which is incorporated herein by reference.

The system 50 further includes a microprocessor controller 400 and a plurality of sensors 500 and sensing circuitry. The microprocessor controller 400 may be computer system that regulates the actuating device 200 and the fluid delivery system 300 (for example, by regulating speed of the actuating device or the amount of fluid pumped through the system) and further may provide power to the actuating device 200 and the fluid delivery system 300. The microprocessor controller 400 works in conjunction with sensors 500, placed throughout the system 50, which provide feedback of the operating conditions of the actuating device 200 and the fluid delivery system 300.

In some embodiments, the microprocessor controller 400 and/or sensors 500 may be configured to integrate control of fluid delivery system 300 to allow for careful control of fluid pump parameters and to allow for adjustment of the pump parameters without user intervention. In some embodiments, the fluid delivery system 300 is separate and operated independently of the microprocessor controller 400.

The microprocessor controller 400 and the sensors 500, in some embodiments, are configured to monitor the operating frequency (i.e., the frequency of the reciprocating motion described herein) of an actuating rod of the actuating device 200, and/or the needle group of the needle cartridge 100. The microprocessor controller 400 and/or the sensors 500 may provide a closed loop control of the frequency to provide for more consistent results by insuring that treatment parameters (e.g., the cycle frequency of the reciprocating motion) are consistent and accurate.

In some embodiments, the microprocessor controller 400 is configured to uniquely identify the actuating device 200 attached to the microprocessor controller 400. The treatment parameters may then be matched to the particular actuating device 200 to ensure consistency of treatment from patient to patient and across varying actuating devices 200.

In some embodiments, the actuating device 200 may be configured to transmit information to the microprocessor controller including, (1) an electronic serial number uniquely identifying each actuating device 200, (2) individual motor turns corresponding to needle oscillations, (3) whether the needle cartridge 100 is engaged with a patient's skin (for example, to trigger automatic on/off operation), (4) an on/off signal from a manual switch on the actuating device 200.

Some embodiments of the system 50 include an actuating device console 410, a fluid pump console 420, and/or an integrated actuating device and fluid pump console which may be connected to and operate the microprocessor controller 400. In some embodiments, the system 50 is configured to generate a pump signal which can synchronize the fluid pump to the reciprocating motion of the needle group of the needle cartridge 100. Some embodiments of the system 50 are configured to monitor the reciprocating motion of the needle group or actuating rod and detect stalling or abnormal resistance in the actuating device.

The needle cartridge 100, the actuating device 200, and the fluid delivery system 300, individually and collectively, include some or all of the features, components, and functionality described below in conjunction with the remaining figures.

Figure 2:
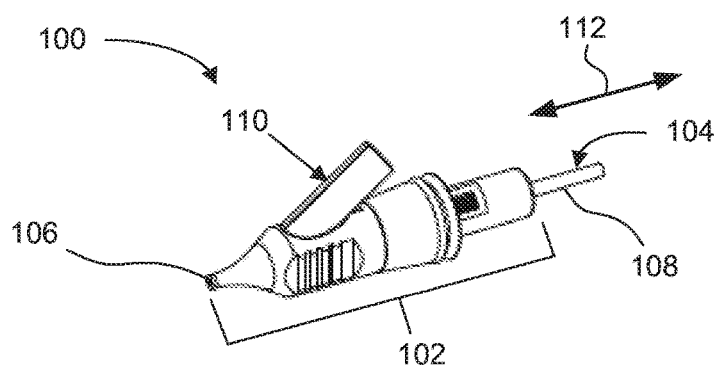
FIG. 2 depicts a perspective view of a needle cartridge for puncturing the epidermis with controlled fluid delivery, according to one or more embodiments of the present disclosure.

Referring to FIG. 2, a perspective view of a needle cartridge 100 for puncturing the epidermis with controlled fluid delivery is shown. In some embodiments, the needle cartridge 100 includes a cartridge housing 102 which forms an internal cavity (not visible). The cartridge housing 102 at least partially encloses a needle group assembly 104 including a needle group (not visible). In the illustrated embodiment, only a shaft 108 (protruding from the cartridge housing 102) of the needle group assembly is visible.

The needle group assembly 104 is configured to move relative to the cartridge housing 102. In the illustrated embodiment, the needle group assembly 104 reciprocates (relative to the cartridge housing 102) in an axial direction (depicted by arrows 112) running along the length of the shaft 108. As the needle group assembly 104 reciprocates relative to the cartridge housing 102, a needle group (not visible) of the needle group assembly reciprocates back and forth at an end opposite the shaft 108.

The needle group reciprocates back and forth and in and out of the cartridge housing 102 through a first aperture 106. The first aperture 106 is located at a tip of the cartridge housing 102 of the needle cartridge 100 on an end opposite where the shaft 108 protrudes from the cartridge housing 102. In the illustrated embodiment, the shaft 108 protrudes out of a second aperture (not visible) of the cartridge housing 102.

Referring to the reciprocating motion of the needle group assembly 104, an end of the needle group emerges from the cartridge housing 102 through the first aperture 106 during a forward motion and retracts back into the cartridge housing 102 through the first aperture 106 during a reverse motion. The needle group moves back and forth between a first position (e.g., a retracted position with the needle group wholly within the cavity of the cartridge housing 102) and a second position (e.g., a forward position with an end of the needle group emerged from the first aperture 106). The needle group is located wholly or at least partially within the cavity of the cartridge housing 102 depending on whether the needle group assembly 104 is in a forward position (e.g., an emerged position) or in a backward position (e.g., a retracted position).

In some embodiments, the cartridge housing 102 of the needle cartridge includes bearings or bearing surfaces that allow the linear reciprocating motion of the needle group assembly 104 and prevents radial motion in a direction away from a longitudinal axis of the needle group assembly 104. The bearing surface may be an inside surface of the cartridge housing 102. In some embodiments, the needle cartridge 100 includes bearings within the cartridge housing 102 that function to allow the linear reciprocating motion of the needle group assembly 104 and prevent radial motion of the needle group assembly 104. In addition, the inside surface of the first aperture 106 prevents radial motion of the needle group and the needle group assembly 104. In some embodiments, the bearings, bearing surfaces, and/or inside surface of the first aperture 106 prevent separation of the needle group in a radial direction.

Although described herein as a needle group, in some embodiments, the needle group assembly 104 includes only a single needle. In some embodiments, the needle group includes a plurality of needles side by side. In some implementations, the needle group includes a grouping of surgically sharpened non-hollow needles. In some embodiments, the needles of the needle group are grouped side by side and are formed in a pattern. In some implementations, the needle group forms a circular pattern at the sharpened end of the needles. In some implementations, the needle group forms a linear pattern at the sharpened end of the needles. The needle group may form any of a number of patterns or shapes and may be designed to form a more particular pattern or shape depending on the need of a user.

In some embodiments, the needle group fully retracts into the cartridge housing 102 through the first aperture 106 during the reciprocating motion. The full retraction of the needle group during the reciprocating motion facilitates various beneficial functions of the needle cartridge 100. In one aspect, during tattoo removal (or during application of a tattoo) the depth of penetration of the needle affects the quality of the removal (or application). For example, penetration either too deep into the skin or too shallow may result in subpar removal (or application) of a tattoo. Penetration too deep into the skin may result in unnecessary scarring. Shallow penetration will not allow ink to be removed during the removal process.

In addition, the tattoo removal technician (or tattoo artist) while moving along the skin in a pattern may catch or snag skin if the needle is inserted into the skin while moving the needle transversely across the skin. In embodiments described herein, the tip of the needle cartridge 100 (i.e., the location of the first aperture 106) may rest on the skin of a patient, allowing the needle group to penetrate the skin at a repeatable depth. In addition, while the needle group is in a fully retracted position, the needle cartridge can by moved transversely to the surface of the skin without catching or snagging the skin. This allows for a far more repeatable process and less training of technicians, as the technician can rest the tip of the needle cartridge on the skin of a patient. In addition, during the tattoo removal process, the reciprocating needle group punctures and break ups the superficial dermal layer of skin to uncover the ink. The tip of the needle cartridge can push the dermal debris aside.

In some embodiments, the needle cartridge 100 is configured to interface with a fluid delivery system. The fluid delivery system may include a fluid reservoir, a pumping system, and a fluid dispenser which is configured to attach to the needle cartridge 100 and deliver fluid into the needle cartridge 100. In some embodiments, the fluid delivery system interfaces with a fluid port 110.

In the illustrated embodiment, the needle cartridge 100 includes a fluid port 110 integrated with the cartridge housing 102. In some embodiments, the fluid port 110 is integral with the housing. In some embodiments, the fluid port 110 attaches to the cartridge housing 102 and forms a seal between the cartridge housing 102 and the fluid port 110. In some embodiments, the needle cartridge 100 is configured to receive fluid into the cavity through the fluid port and discharge fluid from the cavity through the first aperture 106.

The fluid port 110 is a projection that extends away from the cartridge housing 102 at an angle. The projecting fluid port 110 extends away from a longitudinal axis of the cartridge housing 102 (i.e., an axis running from the first aperture 106 to the second aperture of the cartridge housing 102). The vertex of the angle formed between the projecting fluid port 110 and the longitudinal axis is oriented toward the end of the cartridge housing 102 comprising the first aperture 106. That is the opening of the fluid port 110 or third aperture 124 is oriented towards the rear of the needle cartridge 100. In addition, the rear facing fluid port 110 also guides the connecting tube to the rear of the actuating device and away from the tip of the needle cartridge so as to not obstruct the view of the tip or interfere with the puncturing process.

In the illustrated embodiment, the fluid port 110 is a hollow projection extending from the cartridge housing 102 and forming a channel or conduit to the internal cavity of the cartridge housing 102. In some embodiments, the fluid port is a hollow cylindrical projection extending from the cartridge housing 102. The channel or conduit may be any of a number of shapes including a circular cylinder, an elliptical cylinder, a curvilinear cylinder, a polyhedral prism, a combination of a curvilinear cylinder and a polyhedral prism. In some embodiments, the fluid port 110 forms a Luer taper. The taper is designed to allow the insertion of mating connectors (such as a tubing set) and to allow them to be attached with minimal forces while allowing the connection to seal to pressures ranging from 5 psi to 10 psi. The taper further allows the disconnection of the mating connectors with minimal force with no damage or distortion to the taper and mating connectors and further allows, if required, the insertion and sealing of other connectors. For example, a tubing set introduced into the fluid port 110 may form a water tight fitting known as a Luer taper. The angles within the conduit cause the tubing set to be retained in a semi-permanent joint.

The easy connection of the needle cartridge 100 to the fluid delivery system allows the needle cartridge 100 to be easily replaced and allows an operator use a new needle cartridge for each new application.

The fluid port 110 includes a third aperture through which a fluid can be introduced to the internal cavity of the cartridge housing 102 and which ultimately exits from the first aperture 106. In some embodiments, the fluid port 110 includes fluid flow control features. Flow control features may allow fluid to enter the cartridge housing 102 through the fluid port 110 but may also restrict fluid flow from exiting the cartridge housing 102 at the fluid port 110. In some embodiments, the fluid port 110 includes a check valve oriented to allow fluid to enter the cartridge housing 102 and to prevent fluid outflow. Some embodiments may include a flexible elastomeric silicone or rubber diaphragms, flappers, or a duckbill construction, or other known check valves. The valve may be sized be sized to fit the conduit of the fluid port 110. In some embodiments, the flow control features may be a high cracking pressure valve to prevent back flow when the needle cartridge 100 is used with a pressurized fluid flow from a pump.

In some embodiments, the needle cartridge 100 further includes an internal seal (for example, elastomeric) to form a seal between the first aperture 106 and the second aperture. The internal seal restricts fluid flow from exiting the housing at the second aperture. The internal seal forms a seal between the inside surface of the housing and the outer surface of the needle group assembly 104. In some embodiments, the internal seal is attached to the inside surface of the cartridge housing 102 and is further attached to the needle group assembly 104. In some embodiments, the needle group assembly 104 includes a smaller diameter landing area or recessed area onto which the internal seal is attached. The recessed area functions to prevent movement of the internal seal along the length of the needle group assembly 104 during the reciprocating motion of the needle group assembly 104. The internal seal may act as a spring member to bias the needle group assembly 104 in a particular direction. The internal seal may bias the needle group assembly 104 back to an original position after being displaced or driven by an actuating device. In some embodiments, the internal seal, when used in conjunction with a check valve (i.e., in the fluid port 110), can operate as a displacement pump allowing gravity fed fluids fed into the cartridge housing 102 to be displaced out the first aperture 106 of the cartridge housing 102.

Figure 3:
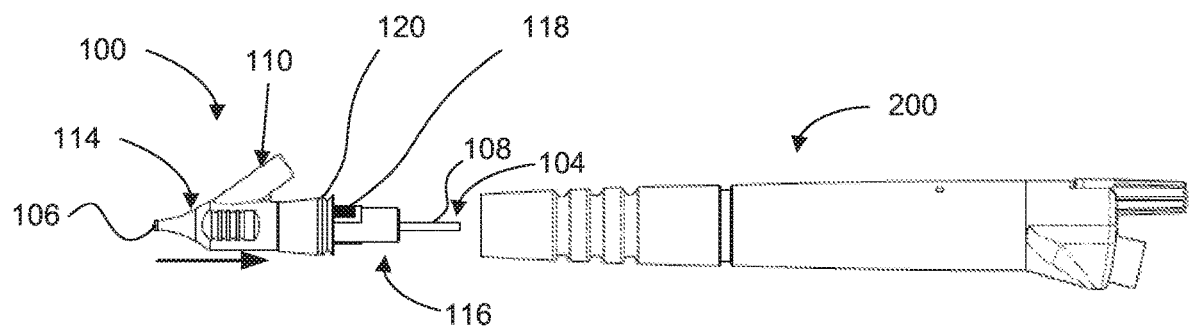
FIG. 3 depicts a side view of a needle cartridge and an actuating device, according to one or more embodiments of the present disclosure.
Figure 4:
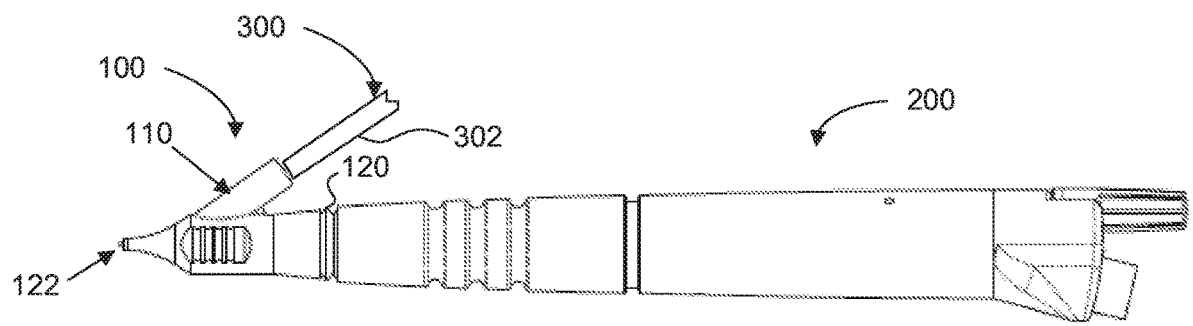
FIG. 4 depicts a side view of a needle cartridge attached to an actuating device, according to one or more embodiments of the present disclosure.
Figure 5:
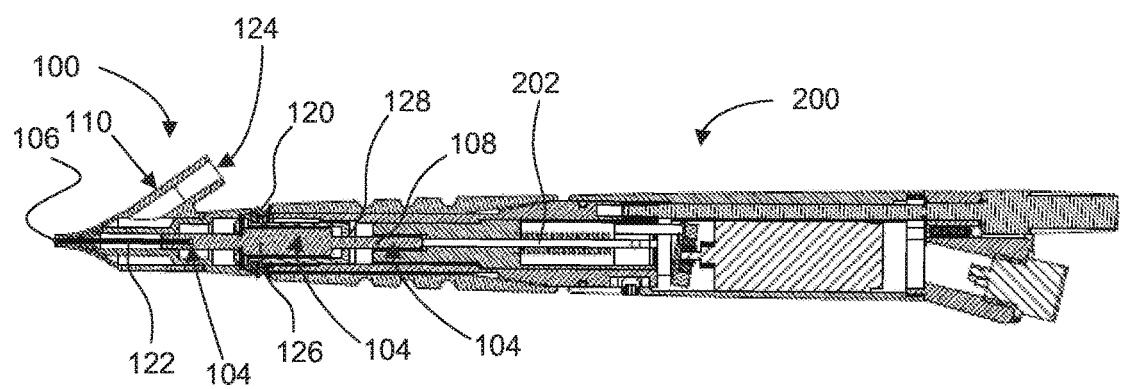
FIG. 5 depicts a cross-sectional side view of a needle cartridge attached to an actuating device, according to one or more embodiments of the present disclosure.

In some embodiments, the needle cartridge 100 is configured to attach to and interface with an actuating device (see e.g., FIGS. 3-5). The actuating device is a mechanical device that physically actuates the needle group assembly 104 and causes the reciprocating motion of the needle group assembly 104 relative to the housing. In some embodiments, the needle cartridge 100 is configured to attach to the actuating device such that the cartridge housing 102 does not move relative to the actuating device. The actuating device may have an actuating rod or other feature which interfaces and moves the needle group assembly 104 in a reciprocating motion. In some embodiments, the cartridge housing 102 includes an interface configured to lock the cartridge housing 102 into the actuating device. In some embodiments, the needle cartridge 100 is configured to attach at an end opposite the first aperture 106. The cartridge housing 102 may include features which interface with the actuating devices (such as clips, notches, seals, etc.).

Although the needle cartridge 100 is shown and described with certain components and functionality, other embodiments of the needle cartridge 100 may include fewer or more components to implement less or more functionality. In addition, each of the components and functionality described in conjunction with FIG. 1 may be applied to each of the remaining figures of the application although not necessarily described herein.

Referring to FIG. 3, a side view of a needle cartridge 100 and an actuating device 200 is shown. The actuating device 200 is a handheld device similar to the actuating device described in conjunction with FIG. 1 and is configured to hold the needle cartridge 100. In addition, the actuating device 200 is configured to actuate a needle group assembly 104 in a reciprocating motion. The needle cartridge 100 is inserted into the actuating device 200 (shown in an attached configuration in FIGS. 3 and 4). In the illustrated embodiment, the needle cartridge 100 includes a tapered end 114 including a first aperture 106 through which a needle or needle group may come forth from an internal cavity (not visible). In some embodiments, the needle cartridge 100 is configured to attach to and interface with the actuating device 200 (see e.g., FIGS. 4-5) at a second end 116 opposite the tapered end 114. The needle cartridge 100 is further configured to interface with a fluid delivery system 300 (see e.g., FIG. 4) at a fluid port 110. The needle cartridge 100 and/or the cartridge housing 102 may include various features 118 which interface and interact with the actuating device 200 to connect and attach the needle cartridge 100 to the actuating device 200.

The illustrated embodiment includes an outer seal 120 that circumferentially surrounds an outer surface of the second end 116 and is configured to interface with an opening of the actuating device 200. The outer seal 120 seals the needle cartridge 100 to the actuating device 200 restricting the ingress of fluid into the interior of the actuating device 200 through the opening. The actuating device 200 interfaces with the protruding shaft 108 of the needle group assembly 104 and actuates the needle group assembly in a reciprocating motion relative to housing of the needle cartridge 100.

Referring to FIG. 4, a needle cartridge 100 is shown attached to an actuating device 200 and a fluid delivery system 300. The fluid delivery system 300 may include a fluid reservoir (not shown), a pumping system (not shown), and a dispenser 302 which is configured to attach to the needle cartridge 100 at the fluid port 110 and deliver fluid into the needle cartridge 100. FIG. 4 depicts the needle cartridge 100 inserted into an opening of the actuating device 200 with the outer seal 120 forming a seal between the cartridge housing 102 and the opening of the actuating device 200.

In the illustrated embodiment, a needle group 122 is shown protruding from the cartridge housing 102 through the first aperture 106. As described above, a needle group assembly 104 is actuated by the actuating device 200 and caused to move in a reciprocating motion. An end of the needle group emerges from the cartridge housing 102 through the first aperture 106 during a forward motion and retracts back into the cartridge housing 102 through the first aperture 106 during a reverse motion. The needle group moves back and forth between a first position (e.g., a retracted position with the needle group wholly within the cavity of the cartridge housing 102) and a second position (e.g., a forward position with an end of the needle group emerged from the first aperture 106). FIG. 4 depicts the needle group in the second position (emerged from the first aperture 106).

The fluid delivery system 300 delivers fluid from the dispenser 302 into a third aperture of the cartridge housing 102 in the fluid port 110 and out the first aperture 106. As the needle group 122 retracts fully into the cartridge housing 102, the first aperture 106 cleans the needle group 122. That is, the interior surface of the first aperture 106 wipes the exterior surface of the needle group 122 during the reverse motion. The fluid delivered by the cartridge may vary depending on the particular function, each having varying properties (e.g., viscosity, etc.) and compositions. In some applications, for example an application using a highly viscous fluid or a fluid that agglomerates, a blockage may form over the first aperture 106. The self-cleaning of the needle group 122 that occurs upon retraction of the needle group 122 into the housing keeps the fluid from agglomerating and blocking fluid flow through the first aperture 106. In addition, dermal debris can sometimes lodge or get stuck in the needle group 122 and/or the first aperture 106. The self-cleaning of the needle group 122 that occurs upon full retraction of the needle group into the housing dislodges the dermal debris.

In addition to the self cleaning of the needle group 122, clogging of the aperture is ameliorated by fluid pressure from the fluid delivery system 300. As described more fully herein, the needle cartridge is sealed with the fluid entering at the third aperture and exiting at the first aperture. The positive pressure applied from the fluid delivery system pushes any clogs from the first aperture. This is possible because the fluid port 110 is sealed to and/or integral with the cartridge housing. In addition, the Luer taper and seal formed therein at the fluid port 110 also allows for the pressure to build and only allow fluid to exit at the first aperture. The sealed housing allows for the pressure to build and only allow the fluid to exit at the first aperture.

FIG. 5 shows a cross-sectional side view of a needle cartridge 100 attached to an actuating device 200. As shown the second end 116 of the needle cartridge 100 is inserted into and interfaces with the actuating device 200. In the illustrated embodiment, the actuating device 200 includes an actuating rod 202. The actuating rod 202 of the actuating device 200 interfaces with the protruding shaft 108 of the needle cartridge 100 and actuates the needle group assembly 104 causing a needle or needle group 122 to reciprocate back and forth and in and out the first aperture 106 of the needle cartridge 100. The fluid delivery system 300 dispenses a fluid into the fluid port 110 through a third aperture 124 of the cartridge housing 102 while the actuating device 200 actuates the needle group 122. The needle cartridge 100 further includes an outer seal 120 that circumferentially surrounds an outer surface of the second end 116 and is configured to interface with the opening of the actuating device 200. The outer seal 120 seals the needle cartridge 100 to the actuating device 200 restricting the ingress of fluid into the interior of the actuating device 200, thereby protecting the actuating rod 202 and other internal components of the actuating device 200.

The fluid enters into the needle cartridge 100 at the third aperture 124 and exits the needle cartridge 100 at the first aperture 106. The fluid exits the first aperture 106 and contacts the skin of the patient while the needle group 122 is reciprocating and penetrating the skin of the patient. The fluid is delivered to the skin to aid in the removal of ink of a tattoo. In the illustrated embodiment, the needle group assembly 104 includes a needle group 122 and a needle holder 126. The needle holder 126 includes the shaft 108 which protrudes out of the cartridge housing 102 through the second aperture 128. The needle holder 126 includes a recessed space on an opposite end to the shaft 108 and holds the needle group 122 together in the recessed space. The needle group 122 may be secured to the needle holder, in some embodiments, by adhesive, insert molding, or other means of attachment. In some embodiments, the plurality of needles in the needle group 122 are welded, brazed, or soldered together. In such embodiments, the needle group 122 is then attached or secured to the needle holder 126.

Figure 6:
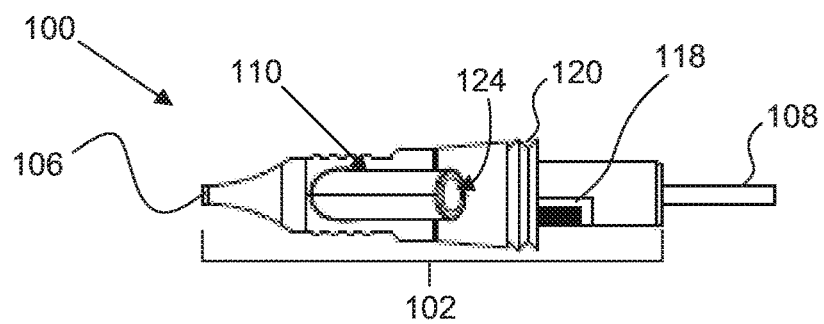
FIG. 6 depicts a top view of a needle cartridge for puncturing the epidermis with controlled fluid delivery, according to one or more embodiments of the present disclosure.
Figure 7:
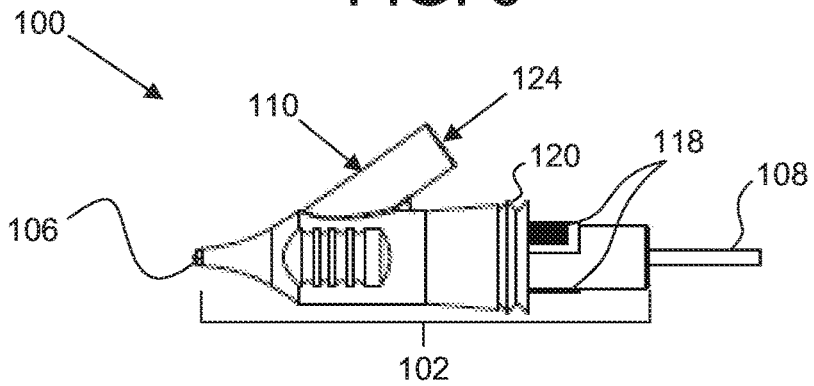
FIG. 7 depicts a side view of a needle cartridge for puncturing the epidermis with controlled fluid delivery, according to one or more embodiments of the present disclosure.
Figure 8:
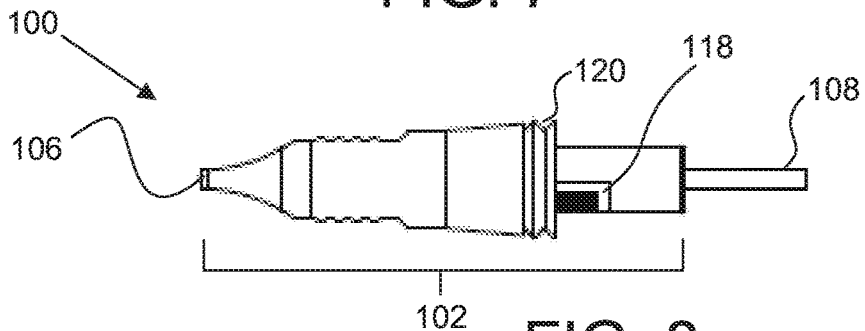
FIG. 8 depicts a bottom view of a needle cartridge for puncturing the epidermis with controlled fluid delivery, according to one or more embodiments of the present disclosure.
Figure 9:
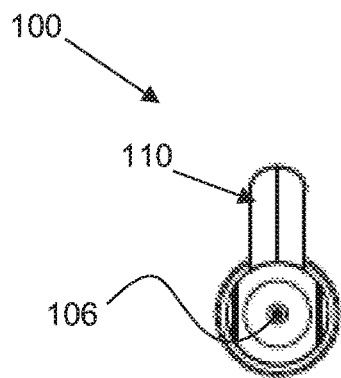
FIG. 9 depicts a front view of a needle cartridge for puncturing the epidermis with controlled fluid delivery, according to one or more embodiments of the present disclosure.
Figure 10:
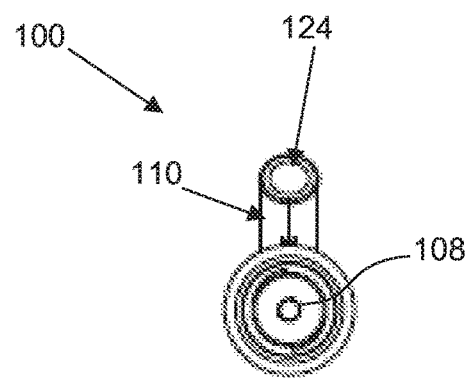
FIG. 10 depicts a rear view of a needle cartridge for puncturing the epidermis with controlled fluid delivery, according to one or more embodiments of the present disclosure.

Referring to FIGS. 6-10, various views of a needle cartridge 100 are shown, according to one or more embodiments of the present disclosure. FIG. 6 shows a top view of the needle cartridge 100 for puncturing the epidermis with controlled fluid delivery. FIG. 7 depicts a side view of a needle cartridge for puncturing the epidermis with controlled fluid delivery. FIG. 8 depicts a bottom view of a needle cartridge for puncturing the epidermis with controlled fluid delivery. FIG. 9 depicts a front view of a needle cartridge for puncturing the epidermis with controlled fluid delivery. FIG. 10 depicts a rear view of a needle cartridge for puncturing the epidermis with controlled fluid delivery.

Figure 11:
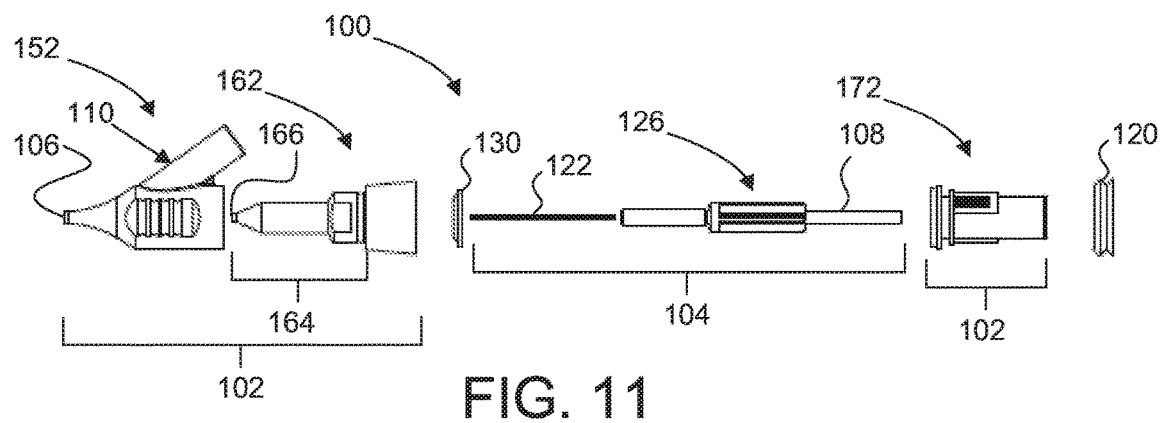
FIG. 11 depicts an exploded side view of a needle cartridge for puncturing the epidermis with controlled fluid delivery, according to one or more embodiments of the present disclosure.
Figure 12:
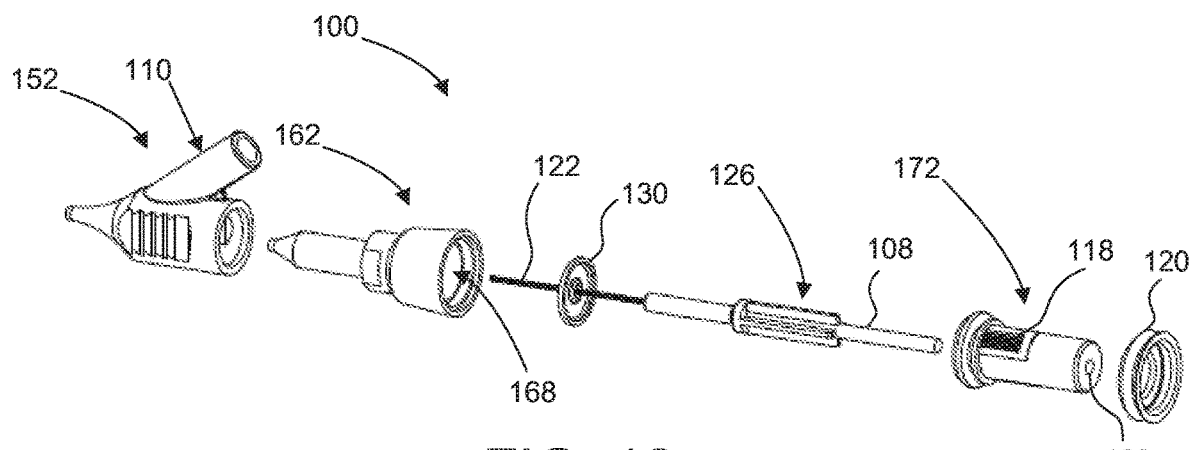
FIG. 12 depicts an exploded perspective view of a needle cartridge for puncturing the epidermis with controlled fluid delivery, according to one or more embodiments of the present disclosure.
Figure 13:
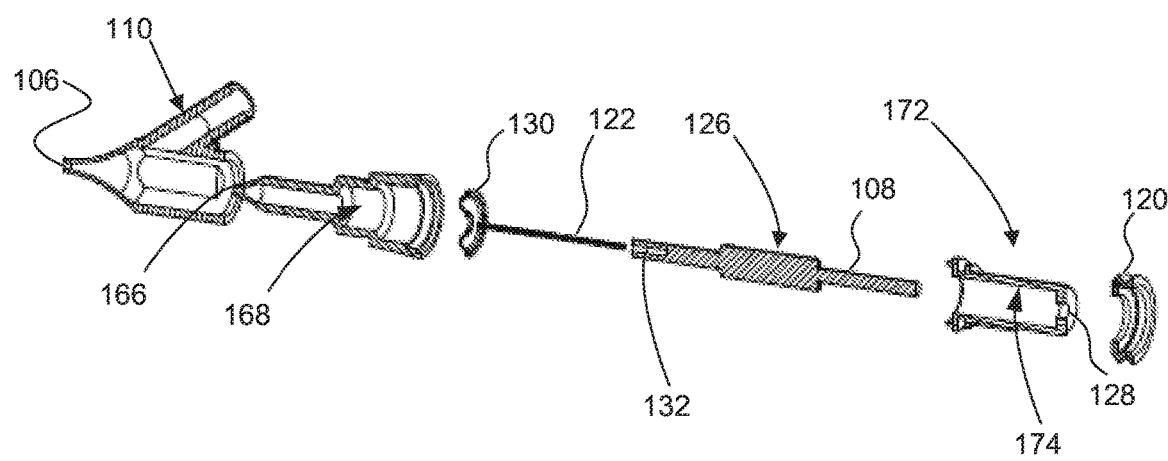
FIG. 13 depicts an exploded cross-sectional view of a needle cartridge for puncturing the epidermis with controlled fluid delivery, according to one or more embodiments of the present disclosure.

Referring to FIGS. 11-13, exploded views of a needle cartridge 100 are shown, according to one or more embodiments of the present disclosure. FIG. 11 depicts an exploded side view of a needle cartridge 100 for puncturing the epidermis with controlled fluid delivery. FIG. 12 depicts an exploded perspective view of a needle cartridge. FIG. 13 depicts an exploded cross-sectional view of a needle cartridge. The needle cartridge 100 includes a cartridge housing 102 and a needle group assembly 104. In the illustrated embodiment, the cartridge housing 102 is formed from separate components including an outer housing 152, a needle group housing 162, and a needle holder housing 172. The outer housing 152, the needle group housing 162, and the needle holder housing 172 connect together to form the cartridge housing 102 and in some embodiments, include some or all the features described in conjunction with the proceeding figures. In other embodiments, the cartridge housing 102 is a single integral piece (see e.g., FIG. 18 and associated description).

In the illustrated embodiment, the outer housing 152 includes the first aperture 106 through which the needle group 122 of the needle group assembly reciprocates and exits the cartridge housing 102. The inner surface of the first aperture 106 is sized to correspond to the outer surface of the needle group 122. In some embodiments, the inner surface of the first aperture 106 is slightly larger than the outer surface of the needle group 122. In such embodiments, the inner surface of the first aperture 106 wipes the outer surface of the needle group 122 during the retraction of the needle group 122 into the cartridge housing 102 through the first aperture 106.

The outer housing 152 forms a cavity into which a portion of the needle group housing 162 fits. The inside surface of the outer housing 152 and the outside surface of the needle group housing 162 forms a fluid cavity (depicted more clearly in FIGS. 14 and 15). The outer housing 152 further includes the fluid port 110. The fluid port 110 may include some or all the features and components described in conjunction with the remaining figures in this specification. The fluid from the fluid delivery system enters the fluid cavity at the third aperture 124 of the fluid port 110 and exits the fluid cavity at the first aperture 106.

The needle group housing 162 forms a needle group cavity 168 in which is housed a portion of the needle group 122. The needle group housing separates the fluid cavity from the needle group cavity 168. The needle group housing 162 further includes a fourth aperture 166 through which the needle group 122 reciprocates. In some embodiments, the needle group 122 not only reciprocates back and forth and in and out the first aperture 106 (similar to what is described above) but also reciprocates back and forth and in and out the fourth aperture 166. In such embodiments, the inside surface of the fourth aperture 166 may function in a manner similar to the first aperture 106 by wiping or scraping fluid off the needle group 122 during the retraction of the needle group. In other embodiments, the needle group 122 is always protruding from the fourth aperture 166 during the reciprocating motion.

In some embodiments, the needle group housing 162 is configured to attach to the outer housing 152 and may snap into the outer housing 152. In some embodiments, the needle group housing 162 and/or outer housing 152 may include various recesses and/or protrusions to allow their attachment together. Some embodiments may further include seals to restrict fluid flow to the above described fluid paths (i.e. into the fluid port 110 and out the first aperture 106.

The needle holder housing 172 forms a cavity in which is housed at least a portion of the needle holder 126. The needle holder housing 172 includes a bearing surface 174 that allows the linear reciprocating motion of the needle group assembly 104 and prevents radial motion. The bearing surface 174 is an inside surface of the needle holder housing 172. The needle holder housing 172 further includes the second aperture 128. The needle holder housing 172 is configured to attach to the needle group housing 162. In some embodiments, the needle group housing 162 and/or needle holder housing 172 may include various recesses and/or protrusions to allow their attachment together. Some embodiments may further include seals to restrict fluid flow from entering the cavity within the needle holder housing 172.

Referring to FIG. 13, a cross-sectional view of the needle holder 126 is shown. In some embodiments, the needle holder 126 includes a recessed space 132 on an opposite end of the needle holder 126 from the shaft 108. The recessed space 132 holds the needle group 122 together in the recessed space. The needle group 122 may be secured to the needle holder, in some embodiments, by adhesive, insert molding, or other means of attachment.

Figure 14:
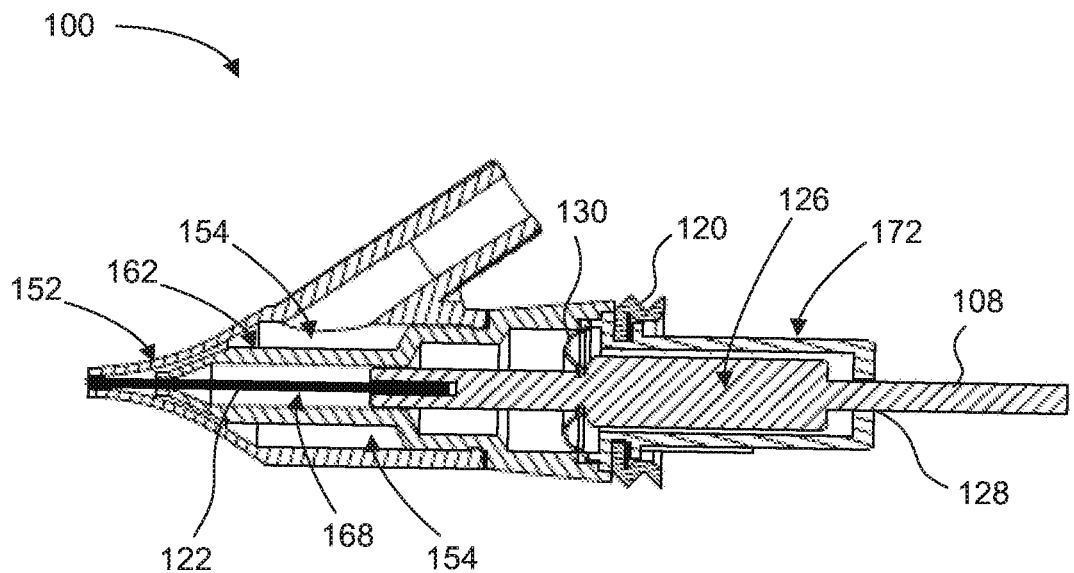
FIG. 14 depicts a cross-sectional side view of a needle cartridge for puncturing the epidermis with controlled fluid delivery, according to one or more embodiments of the present disclosure.

Referring to FIG. 14, the needle cartridge 100 is depicted with the housing formed with the cartridge housing 102 formed. The cartridge housing 102 is formed from the outer housing 152, the needle group housing 162, and the needle holder housing 172. Also depicted in FIG. 14 is the fluid cavity 154 which is a chamber bounded by the inner surface of the outer housing 152 and the outer surface of the needle group housing 162. Also depicted FIG. 13 is the needle group assembly 104 including the needle group 122 affixed into the recessed space 132 of the needle holder 126. The shaft 108 of the needle holder is shown protruding through the second aperture 128. Also depicted are the outer seal 120 and the internal seal 130. The internal seal 130 is shown seated in a smaller diameter recess on the needle holder 126 and further forming a seal between the first aperture 106 and the second aperture 128.

In some embodiments, the needle group housing 162 includes a bearing surface that allows the linear reciprocating motion of the needle group assembly 104 and prevents radial motion. The bearing surface is an inside surface of the needle group housing 162 and is depicted in FIG. 13 with the needle holder abutting the bearing surface of the needle group housing 162.

Figure 15:
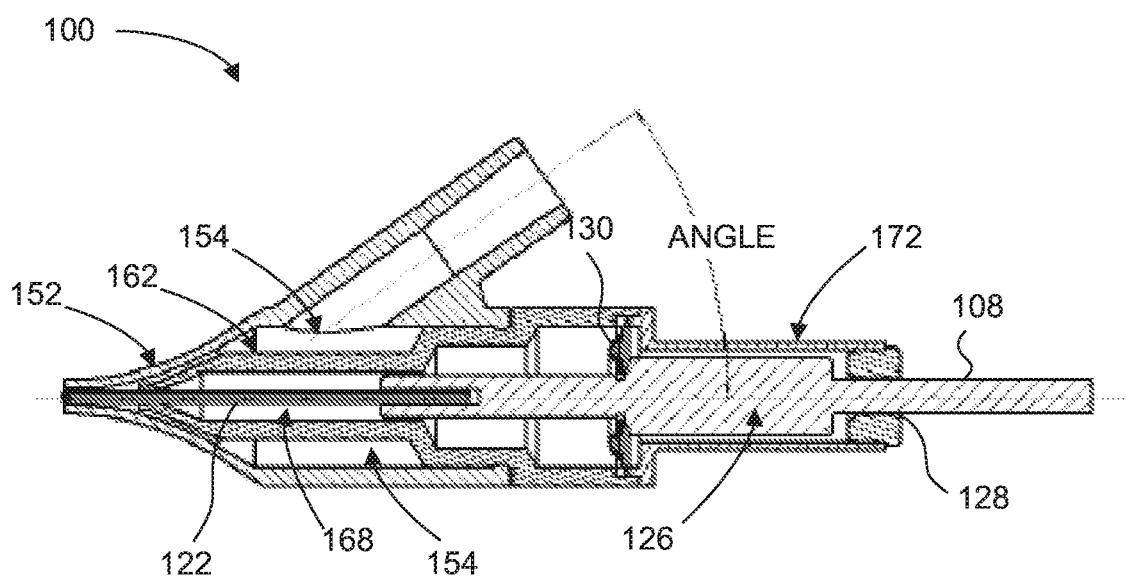
FIG. 15 depicts a cross-sectional side view of a needle cartridge for puncturing the epidermis with controlled fluid delivery, according to one or more embodiments of the present disclosure.
Figure 16:
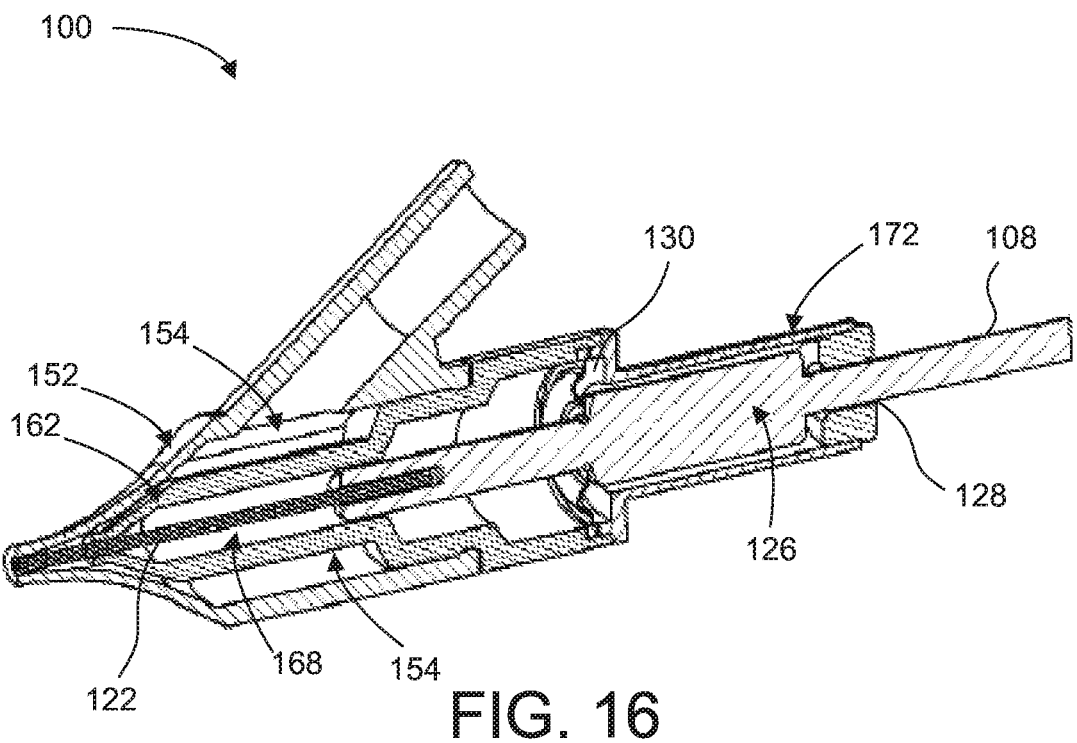
FIG. 16 depicts a cross-sectional perspective view of a needle cartridge for puncturing the epidermis with controlled fluid delivery, according to one or more embodiments of the present disclosure.

FIG. 15 depicts a cross-sectional side view of another embodiment of a needle cartridge 100 for puncturing the epidermis with controlled fluid delivery. FIG. 16 depicts a cross-sectional perspective view of the needle cartridge 100. The features, components, and functionality of FIGS. 15-16 are not described in detail for the sake of brevity, but the needle cartridge 100 of FIGS. 15-16 may include some or all of the features, components, and functionality described in conjunction with FIGS. 1-13. FIG. 15 depicts the angle between the fluid port 110 and the longitudinal axis of the cartridge housing 102 (i.e., the axis running from the first aperture 106 to the second aperture 128. The vertex of the angle formed between the projecting fluid port 110 and the longitudinal axis is oriented toward the end of the cartridge housing 102 comprising the first aperture 106. That is the opening of the fluid port 110 or third aperture 124 is oriented towards the rear of the needle cartridge 100

Figure 17:
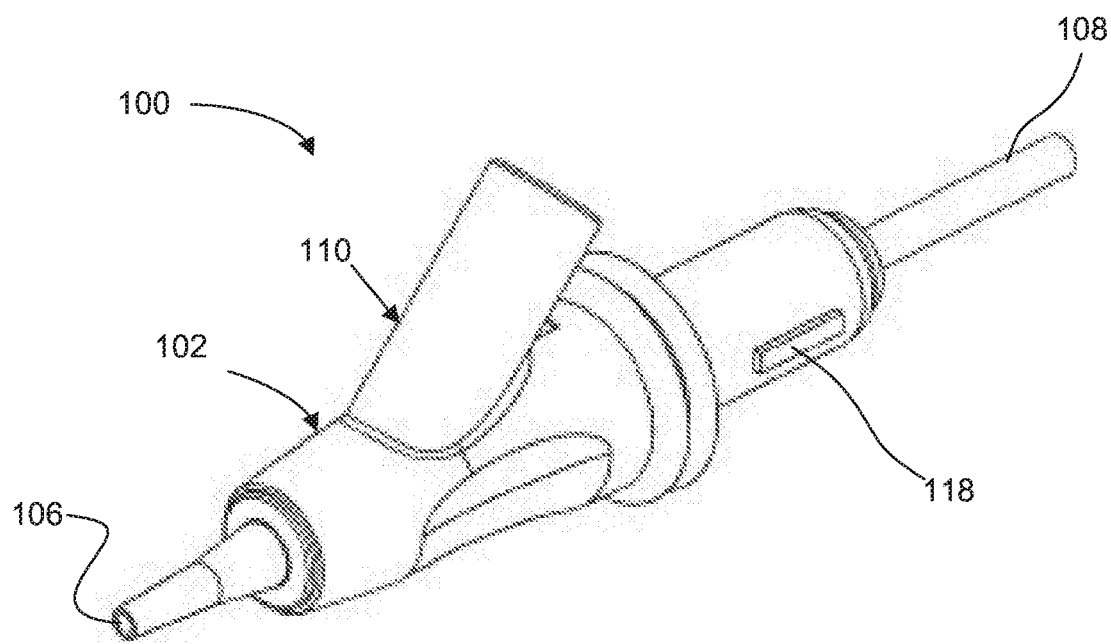
FIG. 17 depicts a perspective view of a needle cartridge for puncturing the epidermis with controlled fluid delivery, according to one or more embodiments of the present disclosure.
Figure 18:
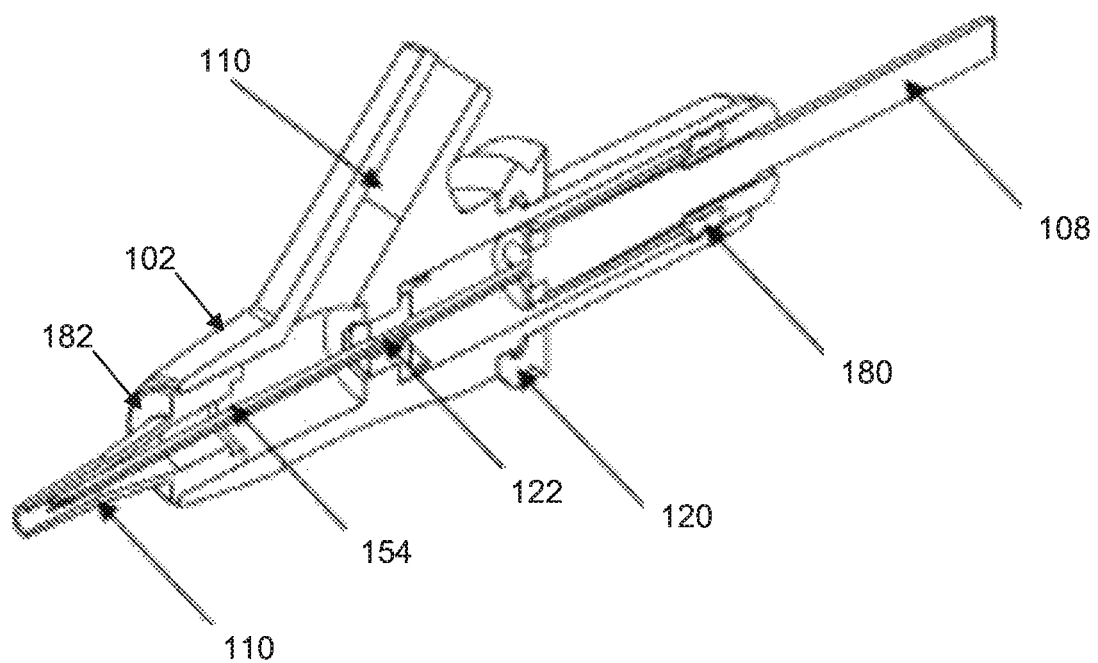
FIG. 18 depicts a cross-sectional perspective view of a needle cartridge for puncturing the epidermis with controlled fluid delivery, according to one or more embodiments of the present disclosure.
Figure 22:
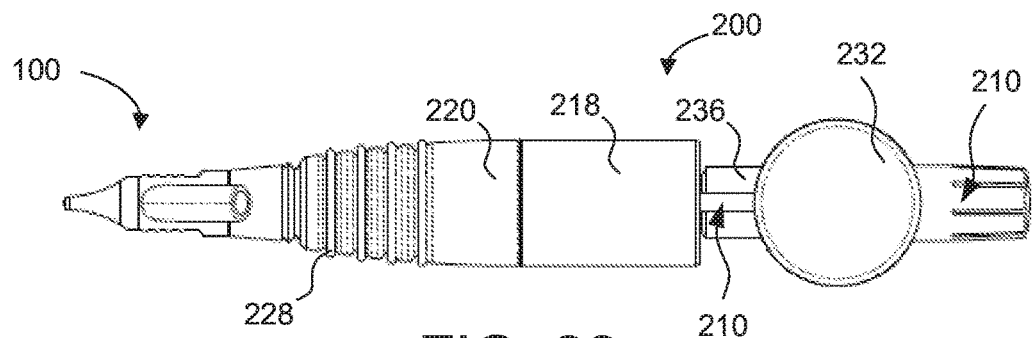
FIG. 22 depicts a top view of an actuating device and an attached needle cartridge, according to one or more embodiments of the present disclosure.
Figure 23:
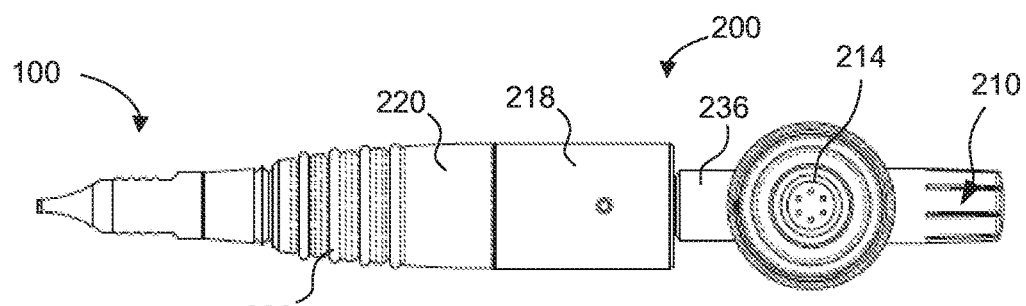
FIG. 23 depicts a bottom view of an actuating device and an attached needle cartridge, according to one or more embodiments of the present disclosure.

FIG. 17 depicts a perspective view of another embodiment of a needle cartridge 100. FIG. 18 depicts a cross-sectional perspective view of the needle cartridge 100. The features, components, and functionality of FIGS. 17-18 are not described in detail for the sake of brevity, but the needle cartridge 100 of FIGS. 17-18 may include some or all of the features, components, and functionality described in conjunction with FIGS. 1-16. Referring now to the FIG. 18, the cartridge housing 102 is a single piece that forms the fluid cavity 154 and includes the fluid port 110. In addition, FIG. 18 depicts a bearing 180 that allows the linear reciprocating motion of the needle group assembly 104 and prevents radial motion. In addition, the needle cartridge includes a nozzle 182 affixed into the cartridge housing 102 which, in some embodiments, forms the first aperture 106. In addition, the nozzle 182 can be replaced or changed in the cartridge housing 102 to accommodate different size and shapes for the first aperture 106, where the size and shape of the first aperture 106 corresponds to the shape and pattern of the needle group 122. For example, if a square needle group 122 is utilized the nozzle 182 can be swapped for a nozzle 182 with a square aperture 106. Multiple nozzles 182 can be used with a same cartridge housing. In addition, the shape of the inside surface of the first aperture 106, in some embodiments, may prevent rotational motion of the needle group 122 and/or needle group assembly 104. Preventing rotational motion of the needle group 104 may be important in non-circular needle groups as rotation of the needle group 104 will result in a different pattern on the skin during needle penetration.

Referring to FIGS. 19-26, an embodiment of an actuating device 200 is depicted. The actuating device 200 is a handheld device and when used in conjunction with the needle cartridge 100 is an apparatus for the puncturing the epidermis with controlled fluid delivery. Although the actuating device 200 is shown and described with certain components and functionality, other embodiments of the actuating device 200 may include fewer or more components to implement less or more functionality.

The actuating device includes an actuating rod 202 housed within a rod housing 208, a motor 204 housed within a motor housing 206, and an adjustment mechanism 210. The motor 204 is configured to drive the actuating rod 202 in a reciprocating motion along a longitudinal axis running the length of the actuating rod 202. The longitudinal axis of the actuating rod 202 is aligned with a longitudinal axis (depicted by dotted line 242) of the rod housing 208.

In the illustrated embodiment of FIGS. 19-26, the rod housing 208 includes an inner rod housing 236 and an outer rod housing. The inner rod housing 236 is affixed to the motor housing 206 and, in some embodiments, does not move relative to the motor housing 206. The outer rod housing is movable relative to the motor housing 206. The outer rod housing translates along the longitudinal axis (depicted by dotted line 242) of rod housing 208. That is, the outer rod housing is movable in a direction away from the motor housing 206 and towards the motor housing 206. The outer rod housing is moved by rotating the adjustment mechanism 210 (described more fully below). The outer rod housing includes an inner cartridge receptacle 218 and an outer cartridge receptacle 220 but, in some embodiments, may be a unitary piece.

In some embodiments, the actuating device includes an actuating rod 202 (see e.g., FIGS. 24-26) configured to oscillate in a reciprocating motion along a longitudinal axis of the actuating rod 202 (e.g., an axis parallel the axis (242) of the rod housing 208). The actuating rod 202 is driven by a motor 204 housed within the actuating device 200. The actuating rod 202 is configured to interface with a needle group assembly 104 of a needle cartridge 100. As the actuating rod 202 oscillates in a reciprocating motion, the actuating rod 202 drives the oscillating motion of the needle group assembly 104 (described above). In some embodiments, the actuating rod 202 interfaces with a protruding shaft 108 of the needle group assembly 104 where the protruding shaft 108 of the needle group assembly 104 extends into the actuating device 200. In alternative embodiments, the actuating rod 202 extends into the cartridge housing 102 of the needle cartridge 100 through the second aperture 128 to interface with the needle group assembly 104. The actuating rod 202, in some embodiments, is configured to be aligned with the needle group assembly 104 when the needle cartridge 100 is attached to the actuating device 200. The actuating rod 202, in some embodiments, is aligned with a device aperture 212 (i.e., the opening where the needle cartridge 100 is attached). The outer rod housing forms the device aperture 212.

The actuating rod 202 may, in some embodiments, include a socket, pin, or other interface mechanism 234 that supports interfacing the actuating rod 202 with the needle group assembly 104. In some embodiments, the actuating rod 202 is configured to only push the needle group assembly 104 and another mechanism (e.g., a spring, etc.) causes the return motion of the needle group assembly 104 during the reciprocating motion. In some embodiments, the actuating rod 202 is configured to attach to the needle group assembly 104 and is further configured to drive the needle group assembly 104 in both directions of the reciprocating motion. The actuating device 200 may include any of a number of mechanical linkages to attach the actuating rod 202 to the needle group assembly 104.

The actuating rod 202 is housed within the rod housing 208 which when combined with other components of the actuating device 200 prevent or restrict the ingress of fluids into the rod housing 208 except through a device aperture 212. Various seals 230 throughout the actuating device 200 are designed to prevent the ingress of fluids into the actuating device 200. The device aperture 212 is fully sealed upon attaching the needle cartridge 100, forming a seal between the device aperture 212 and the outer seal 120 of the needle cartridge 100.

Figure 24:
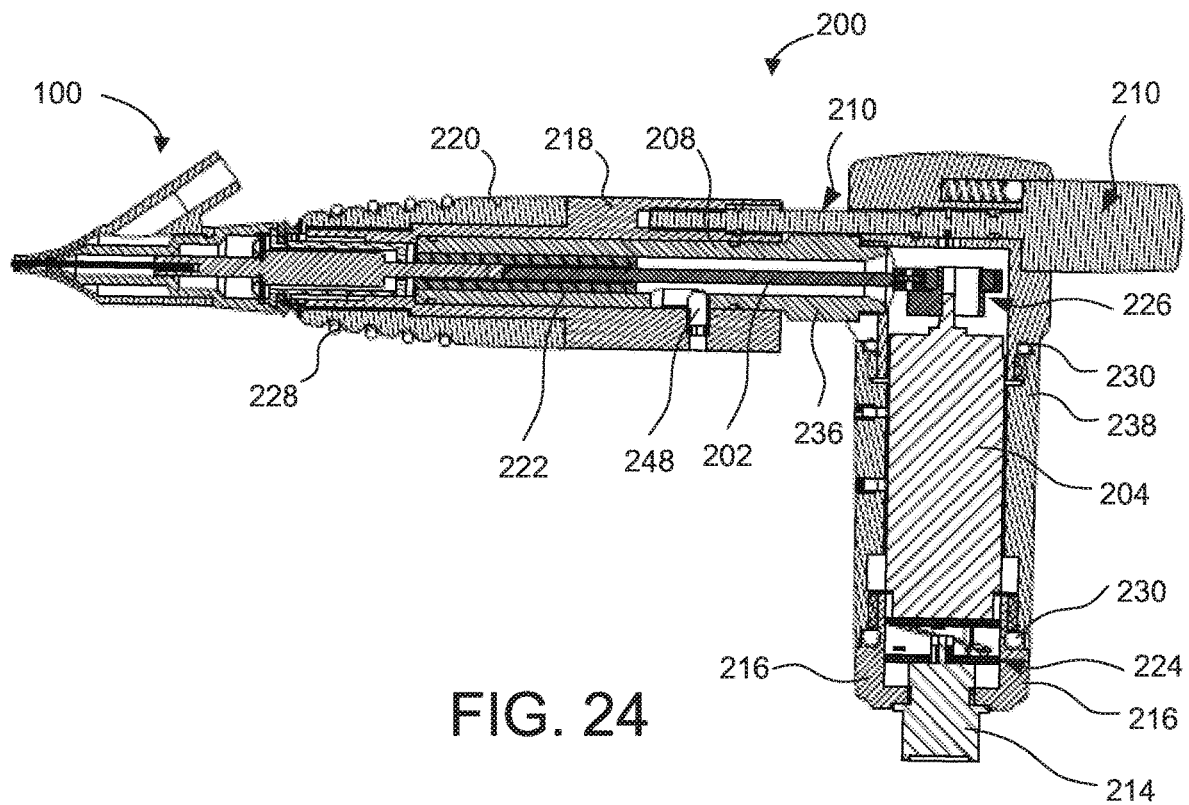
FIG. 24 depicts a side cross-sectional view of an actuating device and an attached needle cartridge, according to one or more embodiments of the present disclosure.

The actuating rod 202 may include a bearing surface configured to limit mechanical noise, limit friction, and limit wear of the rotating and reciprocating components. In some embodiments, the actuating device 200 includes a bearing assembly configured to limit mechanical noise, limit friction, and limit wear of the rotating and reciprocating components. Referring to FIG. 24, the actuating device 200 further includes a bearing guide 222 configured to provide a bearing surface for the actuating rod 202 during the reciprocating motion. In addition, the bearing guide 222 may be configured to provide a bearing surface for the protruding shaft 108 of the needle cartridge 100.

The actuating rod 202 is driven by a motor 204. The motor 204 may be an air driven or electric motor. In some embodiments, the motor 204 is a rotary motor and the actuating device includes a motor linkage mechanism 226 configured to convert rotary motion of a motor shaft into linear reciprocating motion of the actuating rod 202. In some embodiments, the motor linkage mechanism 226 is configured to permanently establish a distance of linear travel of the actuating rod 202 (e.g., based upon a distance of a linear connection pin or crank pin from the axis of the motor shaft). In such embodiments, one rotary revolution of the motor shaft is converted into a single cycle of reciprocating motion of the actuating rod 202. The crank may be attached to the actuating rod 202 to drive the linear reciprocating motion.

The motor 204 is housed within a motor housing 206. In the illustrated embodiment, the longitudinal axis (depicted by dotted line 244) of the motor housing 206 is perpendicular to the longitudinal axis of the rod housing 208. In some embodiments, the angle between the motor housing 206 and rod housing 208 is fixed. In the illustrated embodiment, the angle formed is 90 degrees. Other embodiments may form a larger or smaller angle, for example, between 45 degrees and 135 degrees. In some embodiments, the actuating device 200 is configured such that the motor housing 206 may rest on the back of a user's hand on the skin vertex between the thumb and index finger of the user while the user's fingers may grip the rod housing 208. The actuating device 200 may include grip rings 228 on the outside of the rod housing 208 to aid in gripping the actuating device 200. In some embodiments, the motor housing 206 and the rod housing 208 are made of enough mass to allow the actuating device 200 to diminish the effect of the internal vibrations of the motor 204 and the actuating rod 202 on the housings.

In the illustrated embodiment, the motor housing 206 includes a central housing 238, a motor linkage housing 232, and a socket housing 216. In some embodiments, the motor housing 206 may be a unitary piece. The actuating device includes a power socket 214 and socket interface 224 configured to attach a power cord, electric drive cable, or other type of cord configured to connect the motor 204 to a power source (not shown) external to the actuating device 200. In some embodiments, the power source is the microprocessor controller 400. In some embodiments, the power socket is sealed to not allow the ingress of fluids into the motor housing 206.

Referring back to the outer rod housing. The outer rod housing may include features 272 on an inner surface that are configured to attach the needle cartridge 100. That is, the features 272 of the outer rod housing are configured to interface and interact with the features 118 of the cartridge housing 102. Once attached, the cartridge housing 102 does not move relative to the outer rod housing. In this manner, as the outer rod housing is adjusted relative to the motor housing 206 (and ultimately the actuating rod 202), the cartridge housing 102 will also be adjusted relative to the motor housing 206 (and ultimately the actuating rod 202). By adjusting the outer rod housing and moving it relative to motor housing, the position of the cartridge housing 102 is adjusted relative to the actuating rod 202. That is, the position of the cartridge housing 102 can be adjusted to sit closer to or farther from the actuating rod 202.

As described above, the needle group 122 moves in a reciprocating motion in and out of a first aperture 106 of the cartridge housing 102. The length of extension of the needle group assembly 104 (i.e., how far out of the first aperture 106 the needle group 122 extends) is dependent on where the cartridge housing 102 is seated relative to the actuating rod 202. When the cartridge housing 102 is seated farther away from the actuating rod 202, the length of extension of the needle group assembly 104 is smaller than when the cartridge housing 102 is closer to the actuating rod 202. By adjusting the position of the cartridge housing 102 to sit closer to the actuating rod 202, a user can increase the length of extension of the needle group 122 out the first aperture 106.

By adjusting the position of the outer rod housing relative to the motor housing 206, a user may adjust the position of the cartridge housing 102 relative to the actuating rod 202 and thus may adjust the length of extension of the needle group assembly 104 and ultimately the depth of penetration of the needle group into the skin of a patient.

Typical actuating devices will rotate the barrel housing and by extension the cartridge (as the cartridge is secured to the barrel housing) to adjust the depth of penetration of a needle group into the skin of a patient. Embodiments described herein adjust the length of extension of a needle group without rotating the needle cartridge or the needle group. This is beneficial for many reasons. In one case, where the pattern or shape of a needle group is not round, rotating the needle cartridge and the needle group will rotate the pattern or shape of the needle group as it penetrates the skin. This could be very detrimental to a placement and/or removal process. In another case, if the cartridge rotates relative to the actuating device, the fluid port 110 will rotate. The positioning of the fluid port 110 may be important for the function of a fluid delivery system (whether it is a gravity fed system or pumping system). Changing the orientation of the fluid port 110 may adversely affect the fluid delivery system or result in fluid leaking. In addition, rotating the orientation of the fluid port 110 may be detrimental to a user as the tubing 302 may interfere with the removal process by getting tangled or otherwise impeding the user. Embodiments described herein adjust the depth of penetration of a needle group without rotating the needle cartridge.

Figure 25:
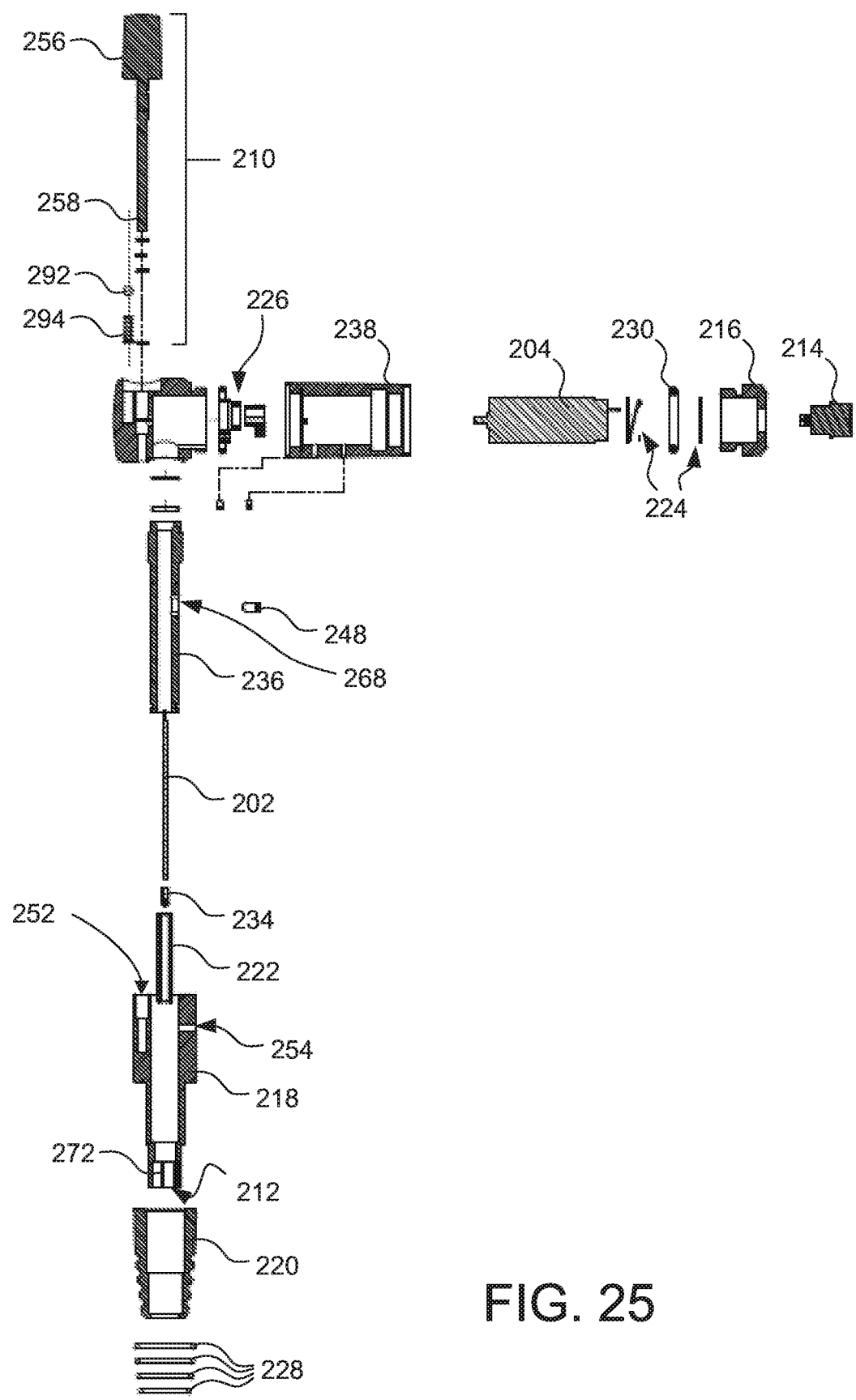
FIG. 25 depicts a side cross-sectional and exploded view of an actuating device, according to one or more embodiments of the present disclosure.
Figure 26:
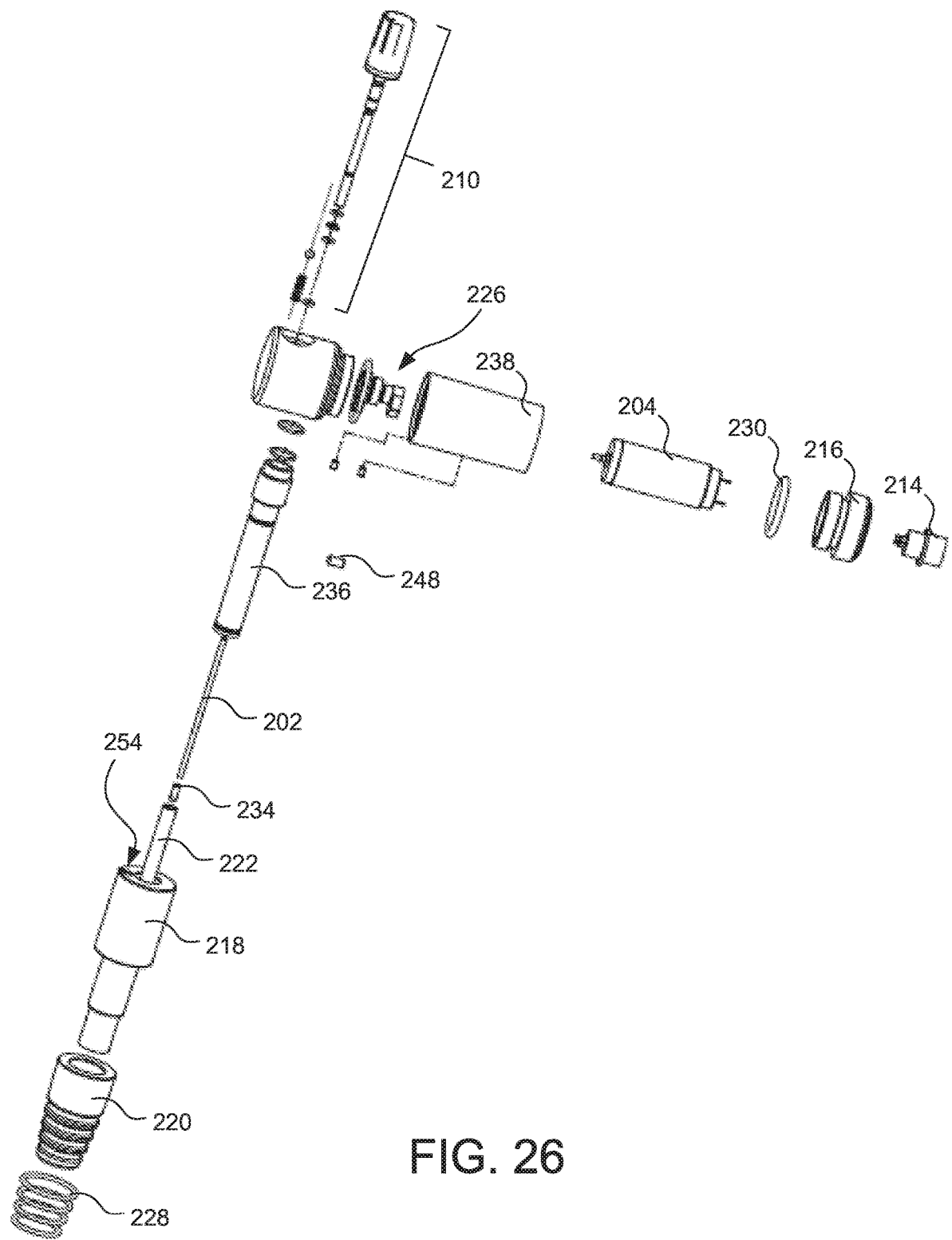
FIG. 26 depicts a perspective exploded view of an actuating device, according to one or more embodiments of the present disclosure.
Figure 27:
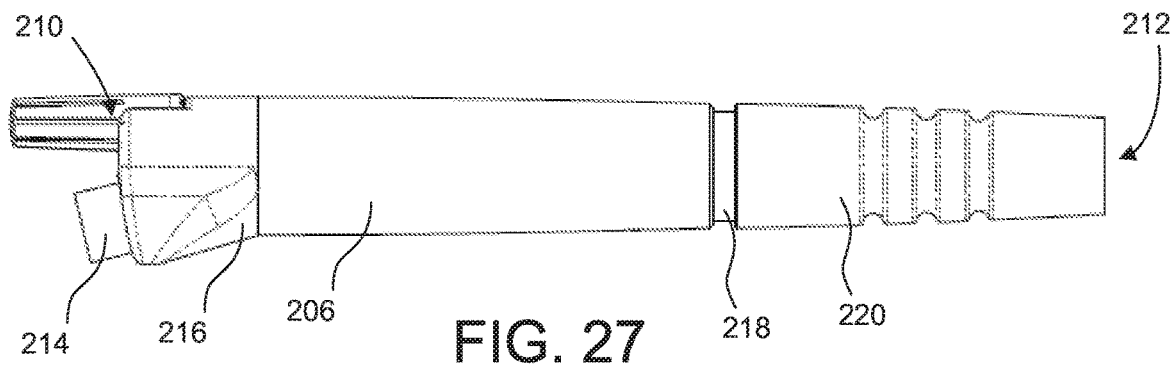
FIG. 27 depicts a side view of an actuating device, according to one or more embodiments of the present disclosure.
Figure 28:
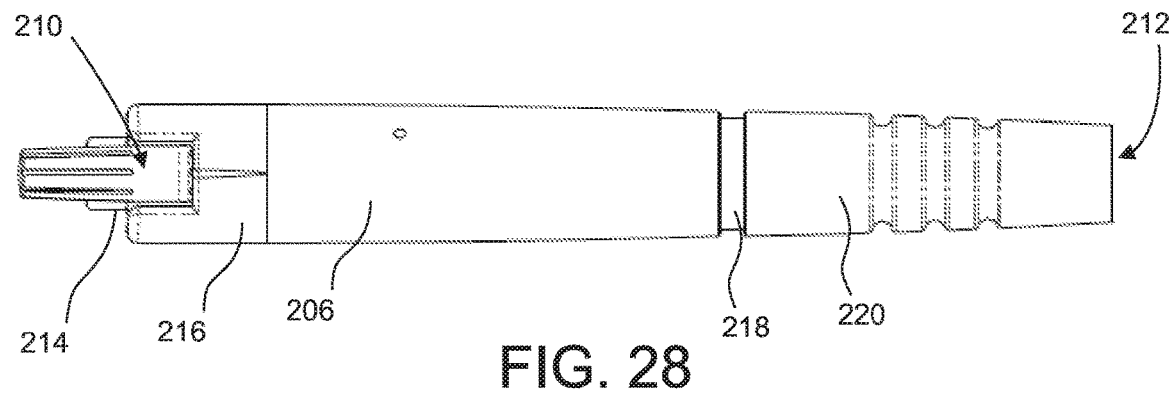
FIG. 28 depicts a top view of an actuating device, according to one or more embodiments of the present disclosure.
Figure 29:
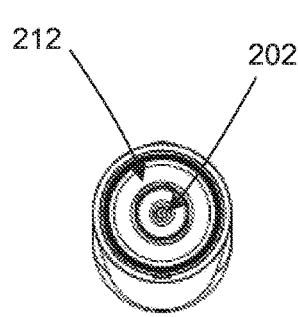
FIG. 29 depicts a front view of an actuating device, according to one or more embodiments of the present disclosure.
Figure 30:
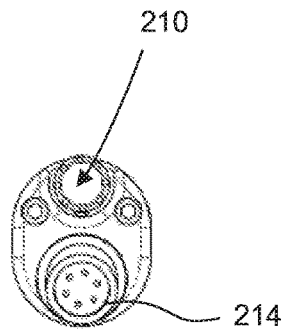
FIG. 30 depicts a rear view of an actuating device, according to one or more embodiments of the present disclosure.

Referring to FIG. 25, the outer rod housing (more specifically, the inner cartridge receptacle 218) includes a mating receptacle 252 at a first end of the inner cartridge receptacle 218. The mating receptacle 252 is configured to receive a threaded end 258 of the adjustment mechanism 210. The adjustment mechanism 210 includes a threaded end 258 and a knob end 256.

Referring to FIG. 24, the adjustment mechanism 210 fits through the motor linkage housing 232 with the knob end 256 extending past the motor linkage housing 232 which allows a user to rotate the adjustment mechanism 210. While the adjustment mechanism 210 is configured to rotate relative to the motor housing 206, the adjustment mechanism 210 does not translate (i.e., does not move along the axis (242)) during the rotation. The opposing end of the of adjustment mechanism 210 (i.e., the threaded end 258) is threaded into the mating receptacle 252 of the inner cartridge receptacle 218. As the user rotates the knob end 256, the threaded end 258 threads into or out of the mating receptacle 252 and thus moves the inner cartridge receptacle 218 relative to the motor housing 206. That is, the position of the outer rod housing (and by extension, the cartridge housing 102) is adjusted relative to the motor housing 206 (and by extension, the actuating rod 202).

Another benefit of embodiments described herein is the placement of the adjustment mechanism 210 on an opposite end of the needle cartridge. In typical configurations, a user adjusts the depth of penetration of a needle group by grabbing and rotating the cartridge itself or near the cartridge. By having the knob end 256 of the adjustment mechanism 210 protruding out of the motor housing 206 at an opposite end of the needle cartridge 100, a user can more easily adjust the depth of penetration of a needle group.

The illustrated embodiment also includes a pin 248 which extends through a hole 254 in the inner cartridge receptacle 218 and into a slot 268 of the inner rod housing 236. The pin 248 restricts the total translation or movement of the inner cartridge receptacle 218 relative to the inner rod housing 236. That is, while the position of the inner cartridge receptacle 218 (and outer rod housing) may be adjusted relative to the motor housing 206, the pin 248 and slot 268 allow only a predetermined amount of movement based on the length of the slot 268.

In some embodiments, the adjustment mechanism 210 may have indentations in a shoulder surface where the knob end 256 and the threaded end 258 meet. The indentations interface with a ball 292 which is pressed into the indentations by a compression spring 294. The ball 292 biases the rotation of the adjustment mechanism 210 to set rotations to allow precise change in position of the outer rod housing. In addition, the set rotations may result in a click upon rotation of the adjustment mechanism 210, allowing a user easily determine the amount of rotation based on the number of clicks made.

Referring to FIGS. 27-33, another embodiment of an actuating device 200 is depicted (see also FIGS. 3-5). The actuating device 200 of FIGS. 27-33, in some embodiments, includes some or all of the features, component, and functionality as described in conjunction with FIGS. 19-26 and are not repeated for the sake of brevity except for a few contrasting features which are described below.

In some embodiments of the actuating device 200, the cylindrical axis of the motor housing 206 (i.e., the central housing 238) is parallel to the cylindrical axis of the rod housing 208 (i.e., the inner rod housing 236 and the outer rod housing). Such embodiments employ a pen-like actuating device that may be easier to handle and maneuver for certain users as opposed to the L-shaped actuating device depicted in FIGS. 19-26.

Referring to FIGS. 27-33, the central housing 238 houses the motor linkage mechanism 226. There is not a separate motor linkage housing 232. In addition, the adjustment mechanism fits through socket housing 216 and central housing 238 and extends out of the socket housing 216. In addition, the inner rod housing 236 is integral with the bearing guide (222) and includes a bearing surface.

Figure 31:
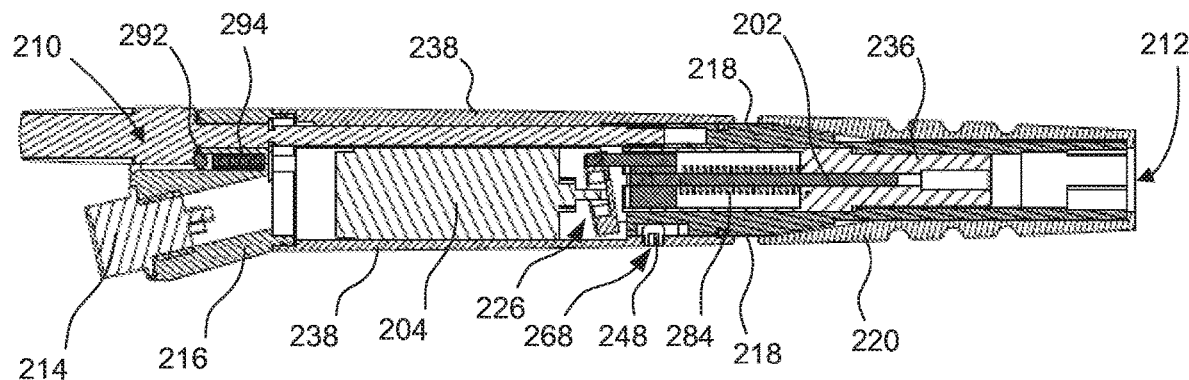
FIG. 31 depicts a side cross-sectional view of an actuating device, according to one or more embodiments of the present disclosure.
Figure 32:
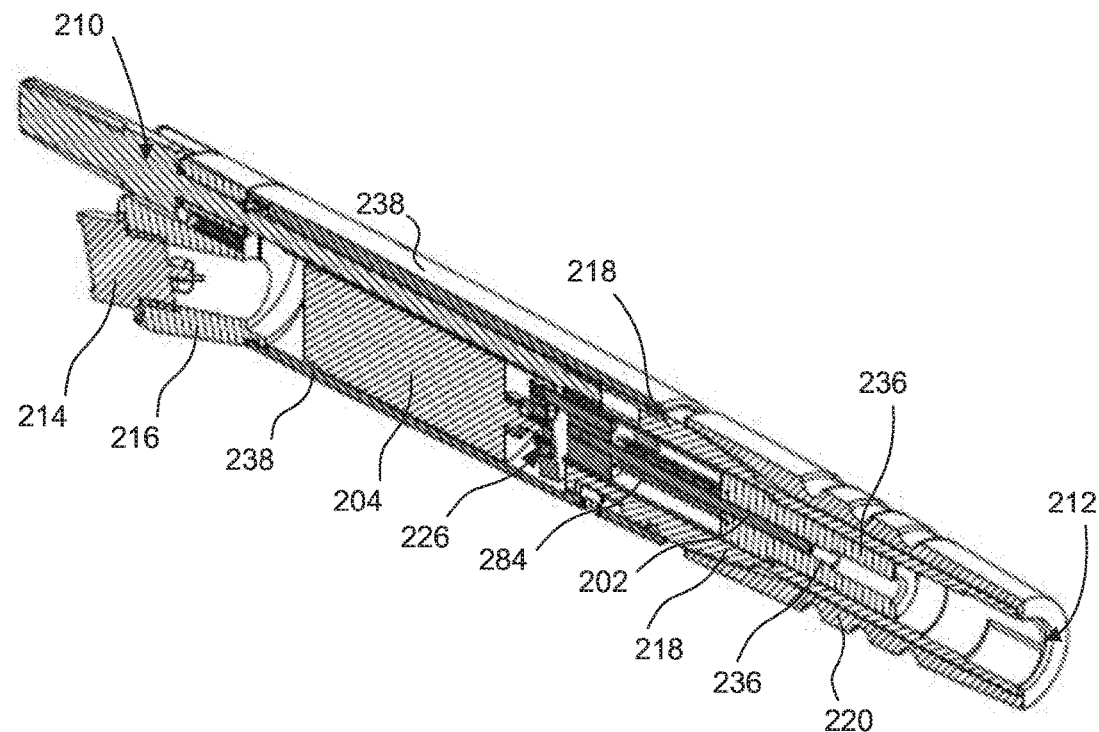
FIG. 32 depicts a perspective cross-sectional view of an actuating device, according to one or more embodiments of the present disclosure.
Figure 33:
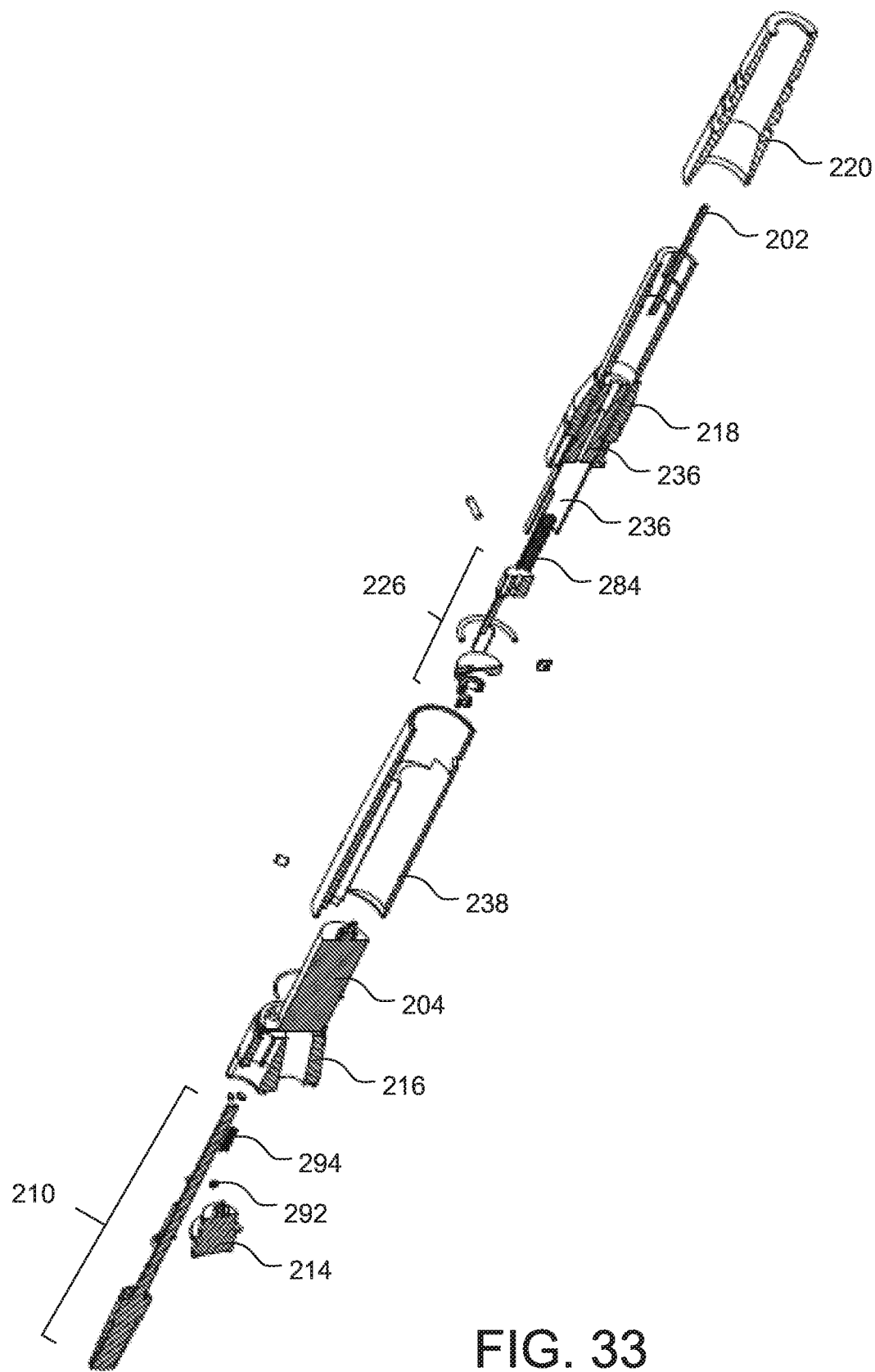
FIG. 33 depicts a perspective cross-sectional and exploded view of an actuating device, according to one or more embodiments of the present disclosure.

Referring to FIG. 31, the illustrated embodiment employs a swash plate mechanism for the motor linkage mechanism 226 to translate rotational motion of the motor shaft into reciprocating motion of the actuating rod 202. The motor shaft of the motor 204 rotates a swash plate which interfaces with the actuating rod 202 and reciprocates the actuating rod 202 as a face surface of the swash plate wobbles during the rotating motion. The actuating device 200 also includes a spring 284 which is compressed and biases the actuating rod 202 back to the face surface of the swash plate to aid in driving the reciprocating motion. Other mechanism may be employed to convert rotational motion of the motor shaft into reciprocating motion of the actuating rod 202.

Figure 34:
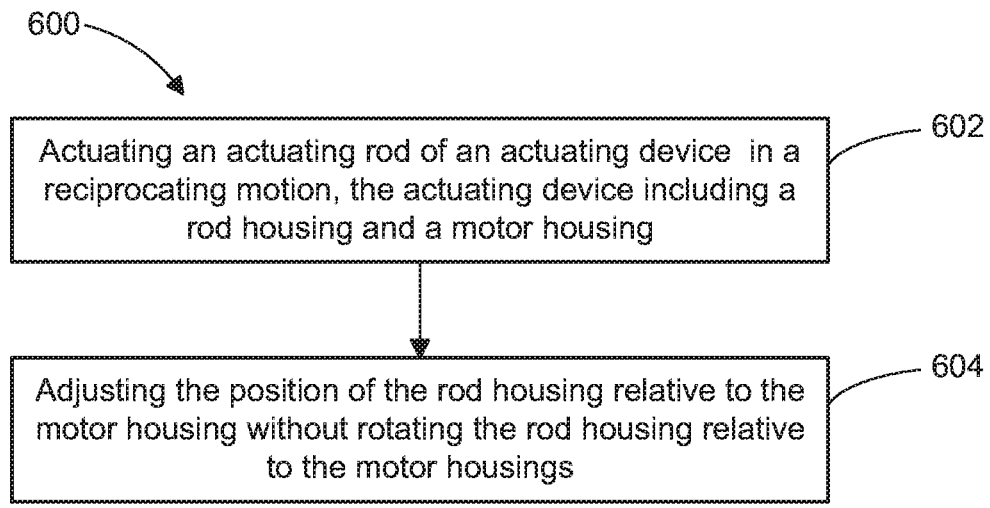
FIG. 34 depicts a flow chart diagram of a method for puncturing an epidermis with controlled depth, according to one or more embodiments of the present disclosure.

FIG. 34 depicts a flow chart diagram of an embodiment of a method 600. Although the method 600 is described in conjunction with the needle cartridge 100, the actuating device 200, and the fluid delivery system 300 of FIGS. 1-33, embodiments of the method 600 may be implemented with other types of apparatuses and systems.

At 602, an actuating rod of an actuating device is actuated in a reciprocating motion. The actuating device may, in some embodiments, include some or all of the features, component, and functionality of the actuating device 200 described herein. At 606 the position of the rod housing of the actuating device is adjusted relative to the position of the motor housing without rotating the rod housing relative to the motor housing. The depicted method 600 then ends. Embodiments of the method 600 may further include some or all of the features, components, and functionality described above in conjunction with FIGS. 1-33 and are not described herein for the sake of brevity.

In the above description, certain terms may be used such as "up," "down," "upwards," "downwards," "upper," "lower," "horizontal," "vertical," "left," "right," "over," "under" and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise. Further, the term "plurality" can be defined as "at least two."

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

As used herein, a system, apparatus, structure, article, element, component, or hardware "configured to" perform a specified function is indeed capable of performing the specified function without any alteration, rather than merely having potential to perform the specified function after further modification. In other words, the system, apparatus, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware which enable the system, apparatus, structure, article, element, component, or hardware to perform the specified function without further modification.

For purposes of this disclosure, a system, apparatus, structure, article, element, component, or hardware described as being "configured to" perform a particular function may additionally or alternatively be described as being "adapted to" and/or as being "operative to" perform that function.

The schematic flow chart diagrams and method schematic diagrams described above are generally set forth as logical flow chart diagrams. As such, the depicted order and labeled steps are indicative of representative embodiments. Other steps, orderings and methods may be conceived that are equivalent in function, logic, or effect to one or more steps, or portions thereof, of the methods illustrated in the schematic diagrams.

Additionally, the format and symbols employed are provided to explain the logical steps of the schematic diagrams and are understood not to limit the scope of the methods illustrated by the diagrams. Although various arrow types and line types may be employed in the schematic diagrams, they are understood not to limit the scope of the corresponding methods. Indeed, some arrows or other connectors may be used to indicate only the logical flow of a method. For instance, an arrow may indicate a waiting or monitoring period of unspecified duration between enumerated steps of a depicted method. Additionally, the order in which a particular method occurs may or may not strictly adhere to the order of the corresponding steps shown.

The present subject matter may be embodied in other specific forms without departing from its spirit or essential characteristics. The described embodiments are to be considered in all respects only as illustrative and not restrictive. All changes which come within the meaning and range of equivalency of the claims are to be embraced within their scope.

In the above description, specific details of various embodiments are provided. However, some embodiments may be practiced with less than all of these specific details. In other instances, certain methods, procedures, components, structures, and/or functions are described in no more detail than to enable the various embodiments of the invention, for the sake of brevity and clarity.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. An actuating device for actuating a needle cartridge and puncturing an epidermis with controlled depth, the actuating device comprising:
   a motor housed in a motor housing;
   an actuating rod driven by the motor in a reciprocating motion;
   a rod housing comprising an inner rod housing and an outer rod housing movable relative to the inner rod housing, wherein the actuating rod is housed in the rod housing, the rod housing forming a device aperture, wherein the device aperture receives a needle cartridge, and wherein the outer rod housing attaches to the needle cartridge and the inner rod housing attaches to the motor housing; and
   an adjustment mechanism comprising a threaded end, a knob end, and a shaft extending between the threaded end and the knob end and passing through a portion of the motor housing, wherein the knob end protrudes beyond an end of the motor housing at an opposite end of the motor housing from the needle cartridge; wherein the adjustment mechanism does not rotate the rod housing relative to the motor housing.

2. The actuating device of claim 1, wherein the adjustment mechanism shaft is parallel to and spaced apart from the actuating rod.

3. The actuating device of claim 1, wherein the adjustment mechanism adjusts a length of extension of a needle group of the needle cartridge out a first aperture of the needle cartridge upon adjustment of the position of the rod housing relative to the motor housing, wherein the actuating device does not rotate the needle cartridge relative to the motor housing upon the adjustment of the position of the rod housing.

4. The actuating device of claim 1, wherein the adjustment mechanism adjusts a position of the needle cartridge relative to a position of the actuating rod.

5. The actuating device of claim 4, wherein the adjustment mechanism adjusts a length of extension of a needle group of the needle cartridge out a first aperture of the needle cartridge upon adjustment of the position of the rod housing relative to the motor housing.

6. The actuating device of claim 1, wherein a longitudinal axis of the motor housing is perpendicular to a longitudinal axis of the rod housing.

7. The actuating device of claim 1, wherein a longitudinal axis of the motor housing forms an angle with a longitudinal axis of the rod housing that is between 45 degrees and 135 degrees.

8. The actuating device of claim 1, further comprising a socket that attaches to an electric drive cable, wherein the socket is sealed.

9. The actuating device of claim 1, wherein the device aperture is located on a first end of the actuating device, wherein the knob end of the adjustment mechanism is located on a second end of the actuating device, opposite the first end, and wherein the motor housing attaches to the rod housing at a position between the device aperture and the knob end.

10. The actuating device of claim 1, wherein the rod housing and the motor housing are sealed to prevent an ingress of fluids into the rod housing and the motor housing.

11. A system comprising:
    an actuating device comprising:
       a motor housed in a motor housing;
       an actuating rod driven by the motor in a reciprocating motion;
       a rod housing comprising an inner rod housing and an outer rod housing movable relative to the inner rod housing, wherein the actuating rod is housed in the rod housing, the rod housing forming a device aperture;
       an adjustment mechanism comprising a threaded end, a knob end, and a shaft extending between the threaded end and the knob end, wherein the adjustment mechanism adjusts a position of the outer rod housing relative to the motor housing, wherein the adjustment mechanism does not rotate the rod housing relative to the motor housing; and
    a needle cartridge attached to and interface with the actuating device, the needle cartridge comprising:
       a cartridge housing forming a cavity and comprising a first aperture and a second aperture opposite the first aperture, the cartridge housing further comprising an outer housing, a needle group housing attached to the outer housing, and a needle holder housing attached to the needle group housing, wherein the outer housing comprises the first aperture, and wherein the needle holder housing comprises the second aperture;
a needle group assembly comprising a needle group and a needle holder, wherein the needle group assembly moves in a reciprocating motion relative to the cartridge housing along an axis from the first aperture to the second aperture, wherein during the reciprocating motion the needle group fully retracts into the cavity through the first aperture; and
wherein the outer housing comprises a fluid port;
wherein the reciprocating motion of the actuating rod drives the reciprocating motion of the needle group assembly; and
wherein the needle cartridge does not rotate relative to the motor housing upon adjustment of the position of the rod housing.

12. The system of claim 11, wherein the shaft is parallel to and spaced apart from the actuating rod.

13. The system of claim 11, wherein the adjustment mechanism adjusts a length of extension of the needle group of the needle cartridge out the first aperture of the needle cartridge upon adjustment of the position of the rod housing relative to the motor housing.

14. The system of claim 11, wherein the fluid port comprises a luer taper.

15. The system of claim 11, wherein a vertex of an angle formed between a fluid port projection of the fluid port and a longitudinal axis of the cartridge housing is oriented toward a forward end of the cartridge housing.

16. The system of claim 11, wherein the rod housing and the motor housing are sealed to prevent an ingress of fluids into the rod housing and the motor housing.

17. The system of claim 11, wherein the cartridge housing outer housing comprises a cavity into which a portion of the needle group housing is inserted.

18. The system of claim 17, wherein the inside surface of the outer housing and the outside surface of the needle group housing form a fluid cavity.

* * * * *